(12) United States Patent
Rich et al.

(10) Patent No.: US 7,348,184 B2
(45) Date of Patent: Mar. 25, 2008

(54) PROTEIN INTERACTION DIFFERENCE MAPPING

(75) Inventors: William E. Rich, Redwood Shores, CA (US); Egisto Boschetti, Croissy sur Seine (FR); Lee O. Lomas, Pleasanton, CA (US); Tai-Tung Yip, Cupertino, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 571 days.

(21) Appl. No.: 10/626,493

(22) Filed: Jul. 23, 2003

(65) Prior Publication Data

US 2004/0146937 A1 Jul. 29, 2004

Related U.S. Application Data

(60) Provisional application No. 60/445,536, filed on Feb. 6, 2003, provisional application No. 60/398,641, filed on Jul. 24, 2002.

(51) Int. Cl.
*G01N 33/543* (2006.01)

(52) U.S. Cl. .......................................... 436/518; 435/4

(58) Field of Classification Search ........ 436/514–548; 435/4–7.95, 283.1–289.1, 810; 422/50–73
See application file for complete search history.

(56) References Cited

U.S. PATENT DOCUMENTS

| | | | |
|---|---|---|---|
| 5,234,811 A * | 8/1993 | Beutler et al. ................ | 435/6 |
| 5,571,729 A | 11/1996 | Nakamura et al. | |
| 5,719,060 A * | 2/1998 | Hutchens et al. ........... | 436/174 |
| 6,225,047 B1 * | 5/2001 | Hutchens et al. ............. | 435/5 |
| 6,265,715 B1 | 7/2001 | Perreault et al. | |
| 6,548,021 B1 * | 4/2003 | Church et al. ............. | 422/68.1 |
| 6,599,728 B2 * | 7/2003 | Morin et al. ................ | 435/194 |

FOREIGN PATENT DOCUMENTS

| WO | WO 01/88528 A2 | 11/2001 |
|---|---|---|
| WO | WO 03/042233 A2 | 5/2003 |

OTHER PUBLICATIONS

Koch, Christian, et al., "A role for Ctr9p and Paf1p in the regulation of $G_1$ cyclin expression in yeast;" 1999; *Nucleic Acids Research*; vol. 27; No. 10; pp. 2126-2134.

Lalev, Atanas, et al., "Ribosomal RNA Maturation in Schizosaccharomyces pombe is Dependent on a Large Ribonucleoprotein Complex of the Internal Transcribed Spacer 1;" 2000; *Journal of Microbiology*; vol. 302; pp. 65-77.

Nelson, Thomas J. et al., "Isolation of Protein Subpopulations Undergoing Protein-Protein Interactions;" 2002; *The American Society for Biochemistry and Molecular Biology, Inc.*; pp. 253-259.

* cited by examiner

*Primary Examiner*—Ann Y. Lam
(74) *Attorney, Agent, or Firm*—Townsend and Townsend and Crew, LLP

(57) ABSTRACT

This invention provides methods and materials for mapping interaction characteristics between components of a multi-component biological complex. The methods involve capturing a multicomponent complex on a solid support and washing the support with a series of elution washes forming a gradient of solute concentrations, and determining whether a particular elution wash eluted a particular component.

35 Claims, 9 Drawing Sheets

PROTEIN INTERACTION DIFFERENCE MAPPING

CROSS-REFERENCE TO RELATED APPLICATIONS

This application is related to U.S. provisional patent application 60/398,641, filed Jul. 24, 2002 and 60/445,536, filed Feb. 6, 2003.

STATEMENT AS TO RIGHTS TO INVENTIONS MADE UNDER FEDERALLY SPONSORED RESEARCH AND DEVELOPMENT

[Not Applicable]

FIELD OF THE INVENTION

The invention relates to the field of mass spectrometry, particularly to the field of protein structural analysis using a combination of retention chromatography and mass spectrometry techniques.

BACKGROUND

Protein-protein interaction is an important way through which proteins carry out their function(s). Currently, there are several methods to detect protein-protein interactions. Among them, co-immunoprecipitation (Harlow and Lane, 1988, Antibodies, a laboratory manual. Cold Spring Harbor Laboratory), yeast two-hybrid screening (Fields and Song, 1989, Nature, 340:245-246) and phage display library screening (Smith, 1985, Science 228:1315-1317) are the most commonly used. However, there are severe limitations in these methods. In co-immunoprecipitation, a protein of interest can be precipitated with its antibody, which is immobilized on beads. Any other protein(s) that co-immunoprecipitated with the protein of interest can be identified by either blotting with its antibody when it is known or purification and sequencing when it is a novel protein. However, this method cannot be applied to large-scale screening of protein-protein interactions.

Yeast two-hybrid screening is a recently developed technique for detecting protein-protein interaction. Although a single yeast two-hybrid screening assay can detect many interacting proteins, it is prone to false positive and false negative results. Moreover, many protein-protein interactions only occur in the presence of additional cellular factors or after posttranslational modifications, which may not be present in yeast. Therefore, yeast two-hybrid screens fails to identify many important protein-protein interactions that only take place in mammalian cells. Phage display screening of protein-protein interaction suffers similar limitations.

Therefore, there is a need in both basic research and clinical medicine for improved techniques, particularly high-throughput techniques, which allow rapid and detailed analysis of multiple proteins and their interactions. Such techniques would be extremely valuable in monitoring the overall patterns of protein expression, protein posttranslational modification, and protein-protein interaction in different cell types or in the same cell type under different physiological or pathological conditions.

SUMMARY OF THE INVENTION

This invention provides methods and articles for characterizing the interaction between components of multi-component biological complex, and, in particular, for detecting differences in the interaction of components between different samples. The methods involve capturing a multicomponent biological complex onto a solid support, such as a bead or biochip, through one of the components, particularly by using a biospecific affinity reagent. Then the complex is washed with a series of buffers of changing (e.g., increasing) stringency. The washes in the series form a gradient characterized by an increasing or decreasing concentration of a solute in the wash solution. The wash solutions are collected. Then the washes are examined to determine whether one of the components of the complex has been washed off in any of the wash solutions. If a component is washed off in a wash of different stringency in one sample versus another, this indicates that the interaction between this component and another component in the complex is different in the two samples. Likewise, after the complex is washed with a series of buffers of increasing stringency, the retained components of the complex can be directly detected. If the retained components of the complex differ after a wash of similar stringency in one sample versus another, this indicates that the interactions within this complex are different in the two samples.

Accordingly, in a first aspect this invention provides a method for creating a profile of interactions between components of at least one multicomponent biological complex for a sample, the method comprising, for each complex: (a) providing an aliquot from the sample, wherein the aliquot comprises the multicomponent biological complex from the sample immobilized on a solid support through a biospecific affinity molecule, wherein the affinity molecule binds a first component of the complex and wherein unbound material has been removed from the solid support; (b) washing the immobilized complex with a first sequence of elution washes, wherein the concentrations of a first solute in each elution wash in the sequence form a gradient of increasing or decreasing concentration; and (c) measuring a second component in the successive elution washes; whereby the profile for a complex from a sample comprises the measurements from the elution washes. In one embodiment the method further comprises after step (b), measuring components of the complex still immobilized on the support through the biospecific affinity molecule, whereby the profile further comprises the measurements of the complex.

In one embodiment, the samples are selected from the group consisting of tissue extracts, cell extracts, blood, urine, lymphatic fluid, in vitro protein expression media and derivatives thereof. In another embodiment the at least one complex is one complex or a plurality of complexes, each bound through a biospecific affinity reagent. In another embodiment, the affinity molecule is immobilized to the solid support before binding the complex. In another embodiment the affinity molecule is selected from an antibody, a single chain antibody, a specific binding fragment of an antibody, an affibody, an enzyme, an enzyme substrate, a receptor, a receptor ligand, a drug, a nucleic acid, or an aptamer. In another embodiment the affinity molecule is bound to the solid support after binding the complex. In another embodiment the solid support is a chromatographic resin. In another embodiment the washes are performed in a flow-through device, such as a microtiter plate, a flow-through column or a flow-through microcolumn. In another embodiment the washes are performed in a non-flow-through device, such as a closed-bottomed microtiter plate. In another embodiment the solid support is a SELDI probe comprising the biospecific capture reagent for capturing the complex attached to a surface of the probe. In another embodiment the unbound material is removed with an initial wash.

In another embodiment the solute is selected from an ion (e.g., a hydrogen ion, a metal ion, the ion of an inorganic atom or molecule, or the ion of an organic molecule), a salt, a detergent, an organic molecule or solvent (e.g., glycerol, acetonitrile, triethanolamine, metcaptoethanol, hexane and the like), a biomolecule or a binding competitor.

In another embodiment the method comprises washing the immobilized complex in a second aliquot of the sample with a second sequence of elution washes, wherein the second solute is different than the first solute. In another embodiment the second component is detected by an optical method, an electrochemical method, atomic force microscopy or a radio frequency method. In another embodiment the second component is detected by mass spectrometry, e.g., affinity mass spectrometry and/or SEND.

In another aspect this invention provides a method comprising: (a) providing a set of biological samples, wherein the set comprises at least two subsets, each subset characterized by a different biological characteristic; (b) creating a profile of interactions between components of at least one multicomponent biological complex for each sample in the set, wherein creating a profile for a complex for a sample comprises: (i) providing an aliquot from the sample, wherein the aliquot comprises the multicomponent biological complex from the sample immobilized on a solid support through a biospecific affinity molecule, wherein the affinity molecule binds a first component of the complex and wherein unbound material has been removed from the solid supports; (ii) washing the immobilized complex with a plurality of successive elution washes, wherein the concentrations of a solute in the successive elution washes form a gradient of increasing or decreasing concentration; and (iii) measuring a second component in the successive elution washes, whereby the profile for a sample comprises the measurements from the elution washes solutions from each aliquot; and (c) comparing the profiles for the samples to detect differences in interaction between components in each subset.

In another embodiment step (b) further comprises, after step (ii) detecting components of the complex still immobilized on the support through the biospecific affinity molecule, whereby the profile further comprises the measurements from the support.

In another embodiment the method further comprises performing steps (i)-(iii) on a second aliquot from the samples, wherein the elution washes comprise a second, different solute and the concentrations of the second solute in the successive elution washes form a gradient of increasing or decreasing concentration.

In one embodiment of this method the different biological characteristics are selected from pathological v. non-pathological, drug responder v. drug non-responder, toxic response v. non-toxic response and progressor to disease state v. non-progressor to disease state. In another embodiment the different biological characteristics are exposure to an inhibitor RNA or non-exposure to the inhibitory RNA.

In another embodiment comparing comprises using the profiles to train a computerized learning algorithm, wherein the computerized learning algorithm generates a classification algorithm that classifies a profile into one of the at least two subsets.

In another aspect this invention provides a method for creating a profile of interactions between components of at least one multicomponent biological complex for a sample, the method comprising, for each complex: (a) providing a plurality of aliquots from the sample, each aliquot comprising the same multicomponent biological complex from the sample immobilized on a solid support through a biospecific affinity molecule, wherein the affinity molecule binds a first component of the complex and wherein unbound material has been removed from the solid supports; (b) washing the immobilized complex in each of the aliquots with an elution wash from a first sequence of elution washes, wherein the concentrations of a first solute in the elution washes of the sequence form a gradient of increasing or decreasing concentration; and (c) measuring at least one second component in each of the elution washes; whereby the profile for a sample comprises the measurements from the elution washes from each aliquot.

In one embodiment the method further comprises after step (b), detecting components of the complex still immobilized on the support through the biospecific affinity molecule, whereby the profile further comprises the measurements from the support.

In another embodiment the method further comprises performing step (b) on a second plurality of aliquots from the sample, wherein the elution washes comprise a second, different solute and the concentrations of the second solute in the successive elution washes form a gradient of increasing or decreasing concentration.

In another aspect this invention provides a method comprising: (a) providing a set of biological samples, wherein the set comprises at least two subsets, each subset characterized by a different biological characteristic; (b) creating a profile of interactions between components of at least one multicomponent biological complex for each sample in the set, wherein creating a profile for a complex in a sample comprises: (i) providing a plurality of aliquots from the sample, each aliquot comprising the same multicomponent biological complex from the sample immobilized on a solid support through a biospecific affinity molecule, wherein the affinity molecule binds a first component of the complex and wherein unbound material has been removed from the solid supports; (ii) washing the immobilized complex in each of the aliquots with an elution wash of a first sequence of elution washes, wherein the concentrations of a first solute in the elution washes of the sequence form a gradient of increasing or decreasing concentration; and (iii) measuring at least one second component in each of the elution washes; whereby the profile for a complex in a sample comprises the measurements from the elution washes from each aliquot; and (c) comparing the profiles for the samples to detect differences in interaction between components in the samples.

In one embodiment the method comprises washing the immobilized complex in a second plurality of aliquots from each sample with one elution wash of a second set of elution washes, wherein the concentrations of a second solute in each member of the set of elution washes form a gradient of increasing or decreasing concentration, and wherein the second solute is different than the solute.

In another embodiment step (b) further comprises, after step (ii) detecting components of the complex still immobilized on the support through the biospecific affinity molecule, whereby the profile further comprises the measurements from the support.

In another embodiment the method further comprises performing steps (i)-(iii) on a second plurality of aliquots from the samples, wherein the elution washes comprise a second, different solute and the concentrations of the second solute in the successive elution washes form a gradient of increasing or decreasing concentration.

In another embodiment the method comprises comparing the profiles for the samples to detect differences in interaction between components in the samples.

In another aspect this invention provides a kit comprising: (a) at least one solid support having means to bind a first affinity molecule or to which a first affinity molecule is bound; (b) at least one sequence of elution washes, wherein the concentrations of a first solute in each elution wash in each sequence form a gradient of increasing or decreasing concentration; and (c) at least one MS probe, wherein the MS probe is different from the solid support. In one embodiment the kit further comprises (d) at least one biospecific affinity molecule, wherein the affinity molecule specifically binds a first component of a first multicomponent biological complex.

In another embodiment the solid support is a chromatographic resin. In another embodiment the kit further comprises a multiwell microtiter plate, such as a drip plate. In another embodiment the kit further comprises a column for chromatography e.g., a glass column. The column can utilize gravity flow, centrifugal flow, or mechanically generated flow. In another embodiment the MS probe is a MALDI probe or a SELDI probe comprising an adsorbent bound to the probe surface and/or an energy absorbing molecule attached to the probe surface. In another embodiment the at least one affinity molecule is a plurality of different affinity molecules and each different affinity molecule specifically binds a first component of a different complex. In another embodiment the at least one MS probe is a plurality of MS probes. In another embodiment the at least one MS probe comprises a plurality of SELDI probes comprising an energy absorbing molecule bound to the probe surface. In another embodiment the at least one MS probe comprises a plurality of SELDI probes comprising an adsorbent bound to the probe surface. In another embodiment the affinity molecule is selected from an antibody, a single chain antibody, a specific binding fragment of an antibody, an affibody, an enzyme, an enzyme substrate, a receptor, a receptor ligand, a drug, a nucleic acid, or an aptamer.

In another aspect this invention provides a kit comprising: (a) at least a first MS probe which is a SELDI probe comprising a reactive surface, wherein the reactive surface can covalently couple a biospecific affinity molecule; (b) at least one sequence of elution washes, wherein the concentrations of a first solute in each elution wash in each sequence form a gradient of increasing or decreasing concentration; and (c) at least a second MS probe, wherein the MS probe is a MALDI probe or a SELDI probe comprising a chromatographic surface. In one embodiment the kit further comprises: (d) at least one biospecific affinity molecule, wherein the affinity molecule specifically binds a first component of a first multicomponent biological complex. In another embodiment the affinity molecule is selected from an antibody, a single chain antibody, a specific binding fragment of an antibody, an affibody, an enzyme, an enzyme substrate, a receptor, a receptor ligand, a drug, a nucleic acid, or an aptamer.

BRIEF DESCRIPTION OF THE DRAWINGS

FIG. 4a depicts an aliquot of a sample in which the multicomponent biological complex is immobilized on a solid support through a biospecific affinity reagent. FIG. 4b depicts the complex immobilized on the support subject to a sequence of washes of increasing stringency. FIG. 4c depicts the step where the collected elution washes are analyzed to measure one of the components of the complex not bound by the affinity reagent.

FIG. 5a depicts multicomponent complexes from a plurality of different samples immobilized on solid supports. FIG. 5b depicts the complexes immobilized on the supports subject to a sequence of washes of increasing stringency. FIG. 5c depicts the step where the collected elution washes are analyzed to measure one of the components of the complex not bound by the affinity reagent.

FIG. 6a depicts multicomponent complexes from a plurality of different samples immobilized on solid supports. FIG. 6b depicts depicts the complexes immobilized on the supports subject to a sequence of washes of increasing stringency. FIG. 6c depicts the step where the collected elution washes are analyzed to measure one of the components of the complex not bound by the affinity reagent.

FIG. 7a depicts an aliquot of a sample in which the multicomponent biological complex is immobilized on a solid support through a biospecific affinity reagent. FIG. 7b depicts placing an aliquot of the immobilized complex into different wells for washing each aliquot with a different series of elution washes, each of which forms a gradient. FIG. 7c depicts the step where the elution washes from each series are collected and analyzed to measure one of the components of the complex not bound by the affinity reagent.

FIG. 8a depicts depicts multicomponent complexes from a plurality of different samples immobilized on solid supports. FIG. 8b depicts placing an aliquot of the immobilized complexes into different wells for washing each aliquot with a different series of elution washes, each of which forms a gradient. FIG. 8c depicts the step where the elution washes from each series are collected and analyzed to measure one of the components of the complexes not bound by the affinity reagent.

FIG. 9a depicts multicomponent complexes from a plurality of different samples immobilized on solid supports. FIG. 9b depicts placing an aliquot of the immobilized complexes into different wells for washing each aliquot with a different series of elution washes, each of which forms a gradient. FIG. 9c depicts the step where the elution washes from each series are collected and analyzed to measure one of the components of the complexes not bound by the affinity reagent.

DETAILED DESCRIPTION

I. Introduction

Figure 1:
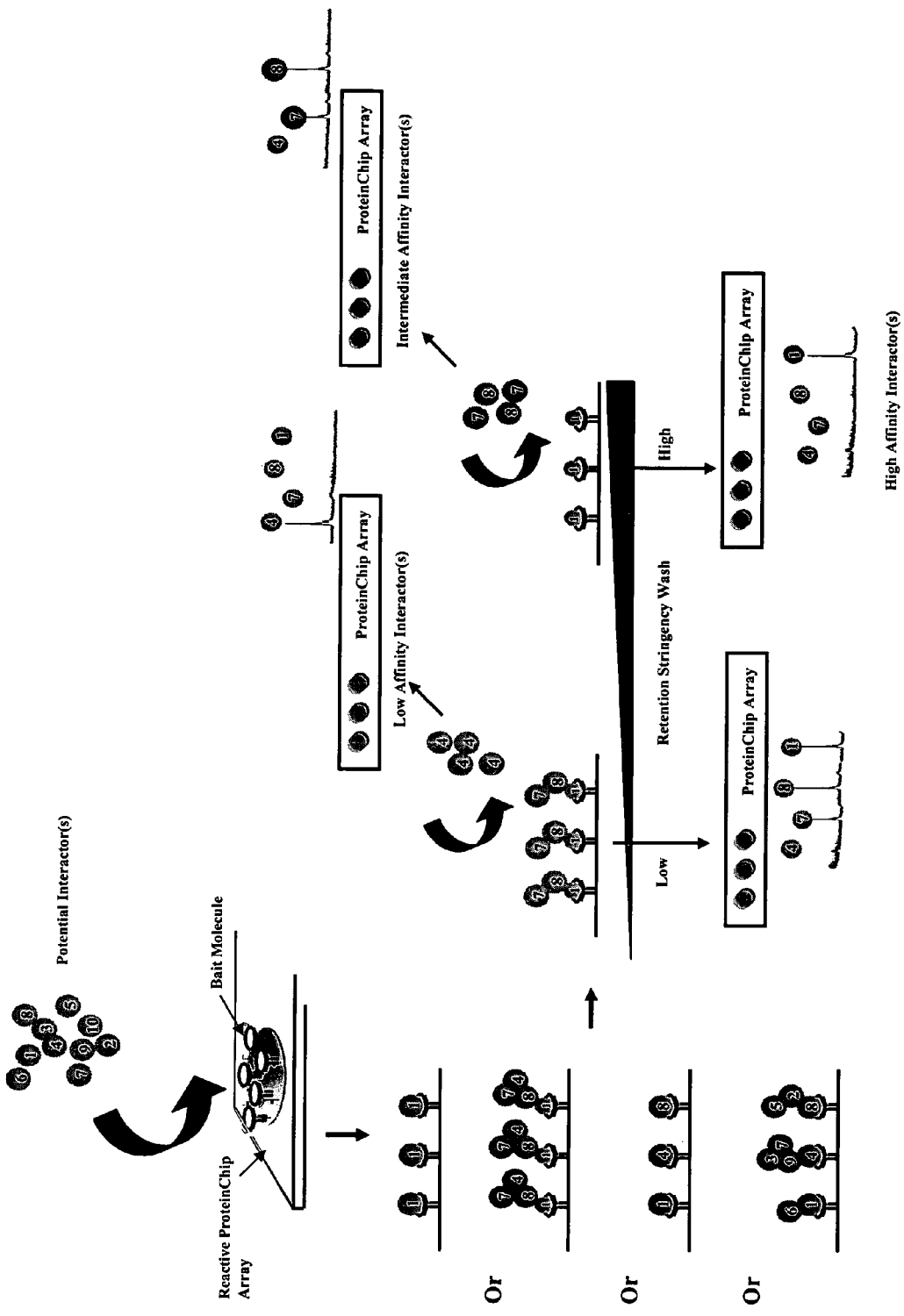
FIG. 1 is a cartoon depicting multicomponent biological complexes binding to immobilized bait molecules. Once bound and immobilized the multicomponent biological complex is depicted as being washed with elution wash solutions of increasing stringency, which differentially dissociates subunits of the complex from the immobilized component. The dissociated subunits are shown being captured on protein chip arrays and analyzed by mass spectrometry. The components of the multicomponent biological complexes that remain bound to the immobilized bait molecules can also be analyzed by mass spectrometry, either in the alternative or in addition to the released components.

This invention provides a method for characterizing interactions between different components of a multi-component biological complex. Biological function, at all levels, relies on in vivo protein-protein interactions. Interactions can be binary, in that a single protein interacts with a second protein, or multifaceted in that multiple proteins interact at single time to form a 'functional unit' (such as TNFa receptor comprised of 6 subunits). This invention focuses on both the binary and multifaceted protein-protein interactions.

The method involves capturing a multicomponent biological complex from a sample on a solid support using a biospecific affinity reagent that specifically binds to one component of the complex. Unbound material is removed, typically with an equilibration buffer. Then, the captured complex is washed sequentially with a series of elution washes in the form of a gradient of increasing or decreasing concentration of a solute, that is to say, of differing stringency, and the wash is collected. Each wash is subjected to analysis to detect an eluted component of the complex that is not bound by the affinity molecule. Eluted components are detected and physical or biochemical properties, such as mass, elemental composition, extinction coefficient, concentration, pI, of the component(s) eluted in successive elution washes are measured.

Alternatively, the retained complex components immobilized can be measured directly or indirectly to create a profile of the retained complex from a sample. In this way, one can determine both the existence of subunits of a multisubunit complex and the stringency of a wash solution under which the component elutes from the complex.

Furthermore, this method can be multiplexed. In such methods, the captured complex may be divided into different aliquots, and each aliquot can be subjected to a series of elution washes in which the gradient is formed by differing concentrations of a solute. Alternatively, different affinity molecules can be used to capture different multicomponent biological complexes from the sample and these complexes can be subjected to the same or different series of elution washes to map component interaction.

This method is important in itself, for detecting various components of a complex. However, it is particularly useful in comparison studies, described below, in which complexes in different classes of samples, for example pathological and non-pathological, are compared to determine whether there is a difference in the character of the interaction between components, as evidenced by differences in how the components elute from the complex. For example, it may be shown that a particular component of a complex binds more tightly to the complex in a non-pathological condition than in a pathological condition, as evidenced by the fact that it requires a more stringent wash to elute the component in non-pathological state than the pathological state.

Advantages of the methods presented in the present invention include speed, ease of use, scanning of multiple interactions simultaneously (high throughput multiplexing), and ability to generate Expression Difference Interaction Maps based on either native protein mass or peptide fingerprint masses (after on-bead enzymic digestion).

Figure 4:
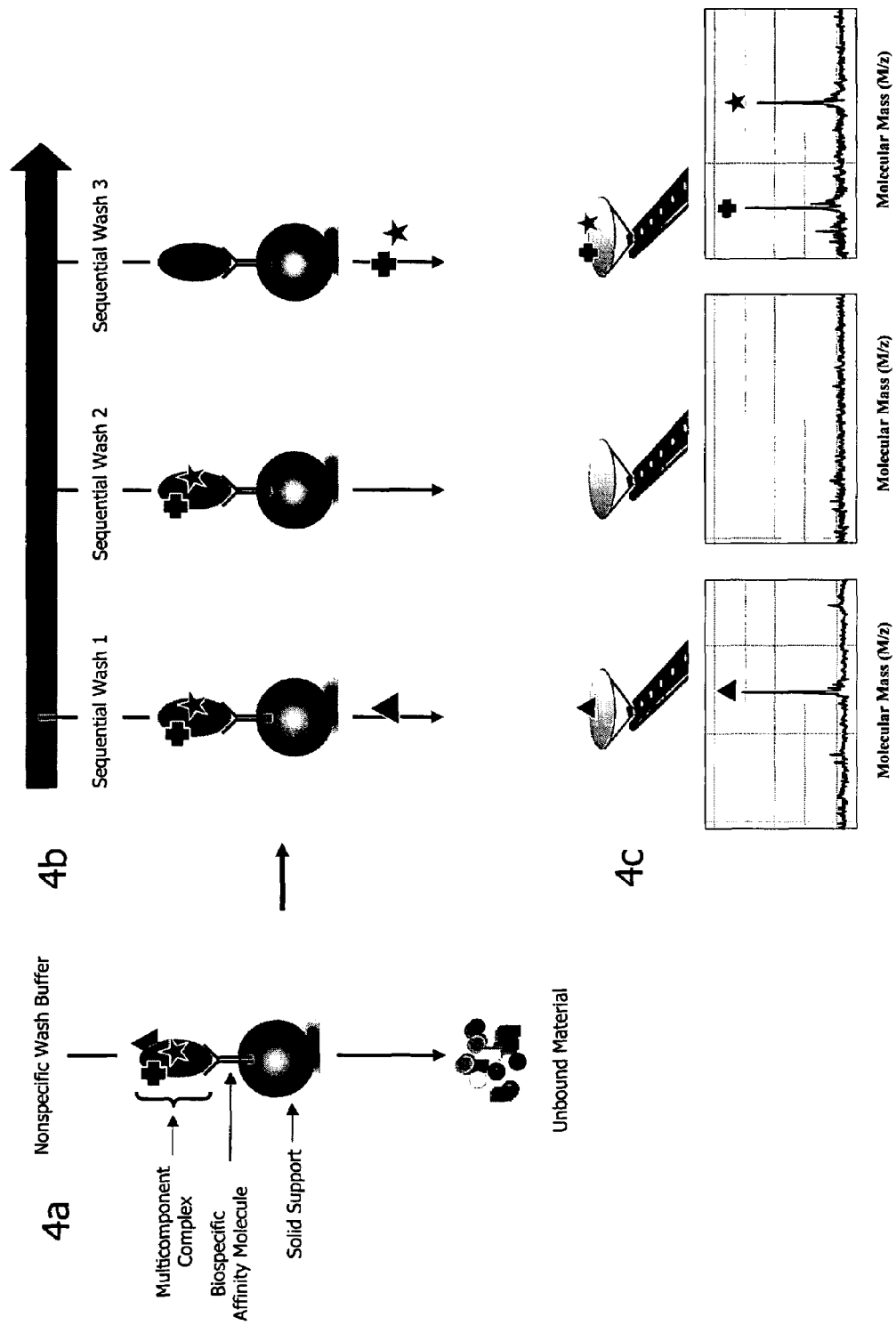
FIG. 4 depicts a method of using a sequential set of elution washes that form a gradient on a single aliquot containing an immobilized multicomponent biological complex to map interactions between components.

Referring to FIG. 4, in step 4a an aliquot of a sample is provided in which a multicomponent biological complex is immobilized on a solid support through a biospecific affinity reagent. Typically, the solid support will be a chromatotographic resin suitable for affinity chromatography. Alternatively, the solid support can be a biochip.

In one embodiment, the method comprises expressing the molecules of the complex in situ, that is, on the surface of the biochip, whereby the complexes are directly captured upon expression/assembly. The molecules also can be expressed in the presence of capture beads or a resin.

The affinity molecule specifically binds one component of the complex. (In the figure, it binds the oval shaped component.) Immobilization to the solid support can be direct or indirect. In direct capture, the solid support is derivatized with the affinity molecule, and the complex is captured from the sample directly on the solid support. In indirect capture, unbound affinity molecule binds to the complex, and then the affinity molecule-with-complex is captured the solid support using, e.g., another capture molecule that binds the affinity molecule. For example, the biospecific affinity molecule could be an IgG molecule and the solid support could be derivatized with protein A, protein G or an anti-IgG antibody.

If the supports are resins or beads, they are conveniently handled in a well of a microtiter plate, which can be a drip plate designed to allow fluid added to the mouth of the well to contact the solid support and then drip our the bottom with any material eluted from the solid support. Alternatively, the resins or beads could be conveniently handled in a column, such as glass or plastic, allowing for either continuous or intermediate flow by gravity, centrifugation, or other type of mechanical or electrical methods. Columns include, for example, spin columns, low pressure chromatography columns and high pressure chromatography columns (e.g., HPLC).

Upon capture, unbound material is removed from the solid support. Typically this is done by washing with an equilibration buffer. However, the unbound material could be allowed to drip off the supports.

In a next step of this embodiment, depicted in FIG. 4, step 4b, the captured complexes are subject to a sequence of washes of increasing stringency. The washes form a sequence of at least two washes (in this example, three washes). Together, the washes in the sequence form a gradient of differing stringency. More specifically, the washes in the sequence will differ by the concentration of a particular solute in the wash. For example, the sequence can increase or decrease according to ionic strength based on an increasing or decreasing concentration of salt in an aqueous buffer. A series of washes of increasing concentration might be 0.1 N NaCl-0.2 N NaCl-0.4 N NaCl. A series of washes of decreasing concentration might involve a metal ion required for binding, such as decreasing concentrations of copper or magnesium. As described below the solute can be one that alters the stringency of the wash solution based on ionic interaction (both ionic strength and pH), water structure, hydrophobic interaction, chaotropism or affinity interaction (e.g., a molecule that competes with a component for binding with another component). Alternatively, the series of washes can differ in the concentration of a plurality of solutes. These washes may or may not elute one of the components from the complex. However, by providing a sequence of washes, one can test the stringency necessary to elute a particular component. The washes are collected for further analysis.

In a next step of this embodiment, depicted in FIG. 4, step 4c, the collected elution washes are analyzed to measure one of the components of the complex that was not bound by the affinity reagent. Measuring can be qualitative or quantitative. For example one could merely determine the presence or absence of the component in one of the washes. Alternatively, one could measure roughly whether the amount of the component in the solution is "high" or "low" compared with some standard. Alternatively, the amount of the component can be quantified more specifically based on the detection method used.

In another embodiment, the components remaining on the solid support can be detected at any step of the elution process. In a preferred embodiment, the solid support is a biochip, such as a mass spectrometry probe, and the retained components are detected by affinity mass spectrometry. When the solid support is a bead, the retained components can be eluted using a high stringency wash, and detected in the wash by the methods described below.

The components can be measured in the elution washes using any detection method of choice, such as a gas phase ion spectrometry method, an optical method, an electrochemical method, atomic force microscopy and a radio frequency method. However mass spectrometry, a form of gas phase ion spectrometry, is particularly useful. Because mass spectrometry provides both detection and the mass of an analyte, analytes can be differentiated based on their mass signature. That is, one can determine whether a particular component is present in an elution wash based on the presence of signal corresponding to the mass of the component.

Any form of mass spectrometry may be used. However, MALDI and SELDI are particularly useful. In particular, components can be conveniently detected using SELDI probes having a chromatographic surface determined to best capture the analyte.

Figure 2:
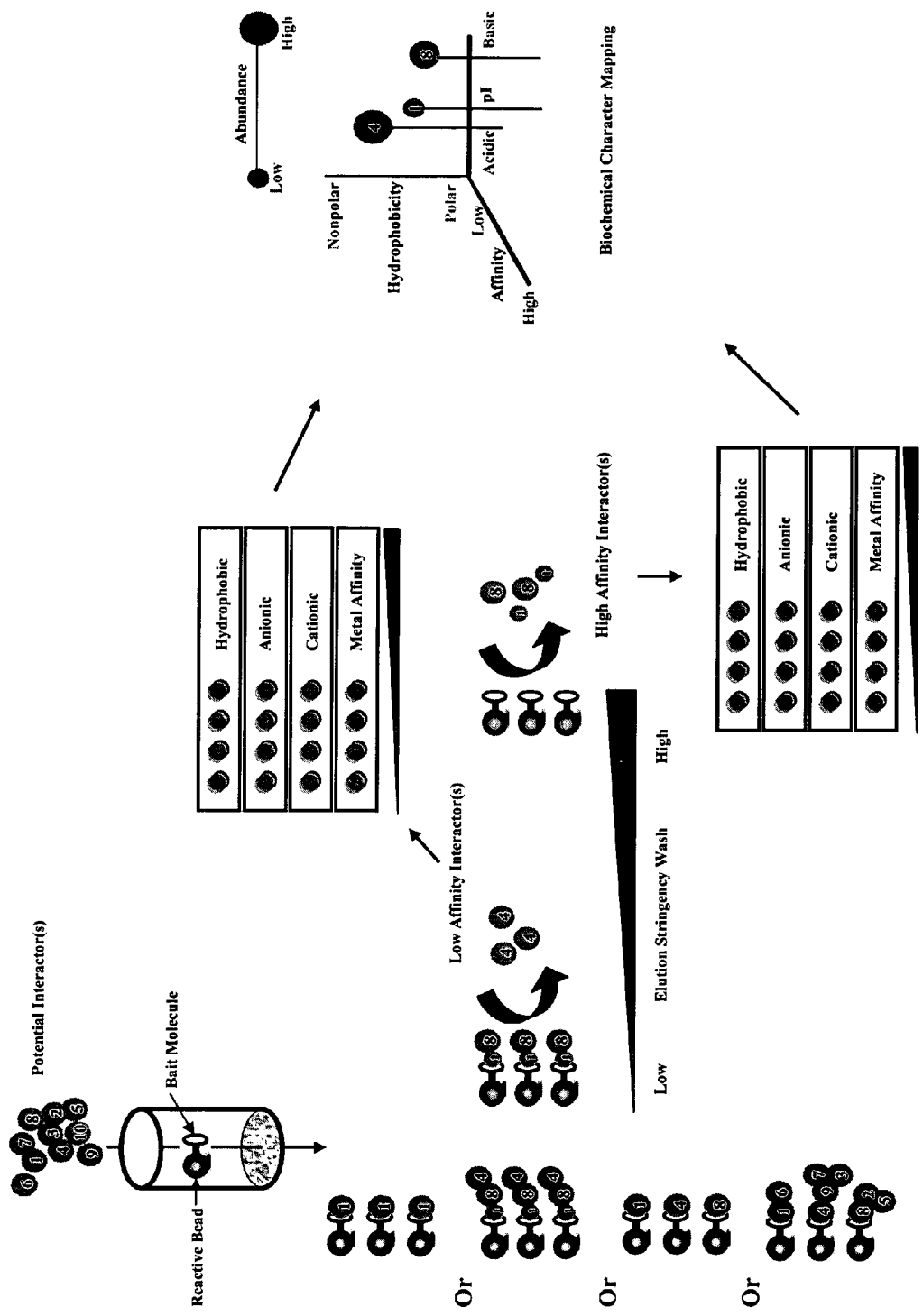
FIG. 2 depicts a methodology for producing a biochemical character map that illustrates the type of molecular interactions that are present within the multicomponent biological complex being analyzed.
Figure 3:
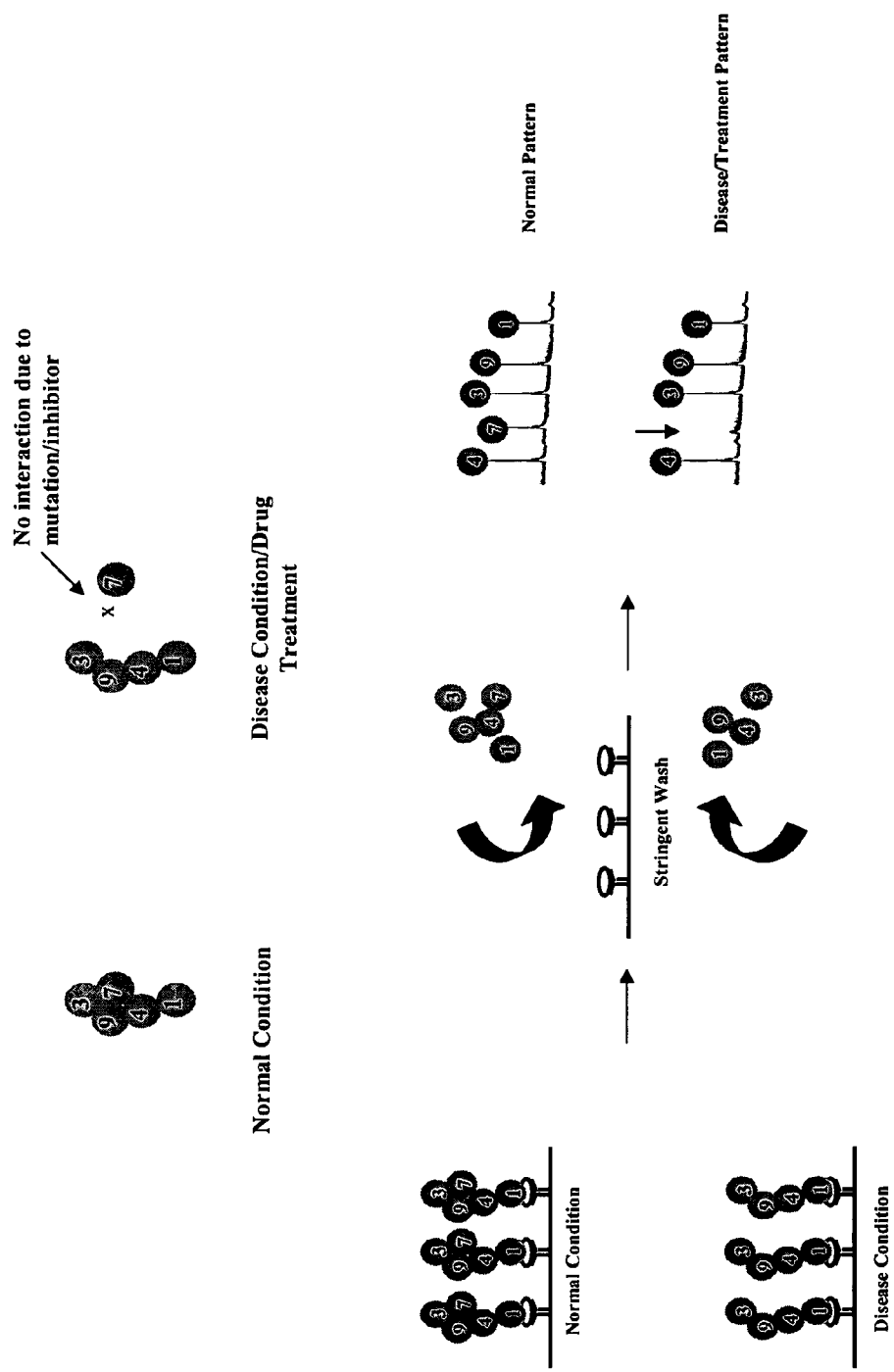
FIG. 3 depicts a methodology that allows for diagnosis of a disease state based upon molecular interactions within a multicomponent biological complex. In the figure, a multicomponent biological complex from diseased tissue is depicted as missing a component that is present in the disease-free state due to an alteration in the nature or amplitude of the biomolecular interactions within the multicomponent biological complex. It will be appreciated that disease states can result from increases as well as decreases in binding, or in aberrant binding of components due to changes in affinity.

The multicomponent biological complex can be usefully tested using a plurality of elution gradients that each differ according to solute. For example, the interaction of the components can be tested based on a pH gradient, a salt gradient and a detergent gradient. The data generated produces a matrix constituting a profile or map of interactions. (See, e.g., the map of FIG. 2.) Such a matrix could include cells that include, for each component, the amount of component detected in each elution wash. The resulting component (e.g., protein) interaction map provides a characterization of the interaction of components in the particular sample tested.

The method described here is particularly useful for component interaction difference mapping. Interaction difference mapping is useful to determine whether the interaction of components differs between samples characterized by different phenotypes. Essentially, the method in this embodiment comprises generating component interaction maps for the components of interest using the method above on both of the different samples, and comparing the maps to determine differences in interaction between the components. This method is depicted in FIGS. 5 and 6, which show the same process, but yielding different results.

Figure 5:
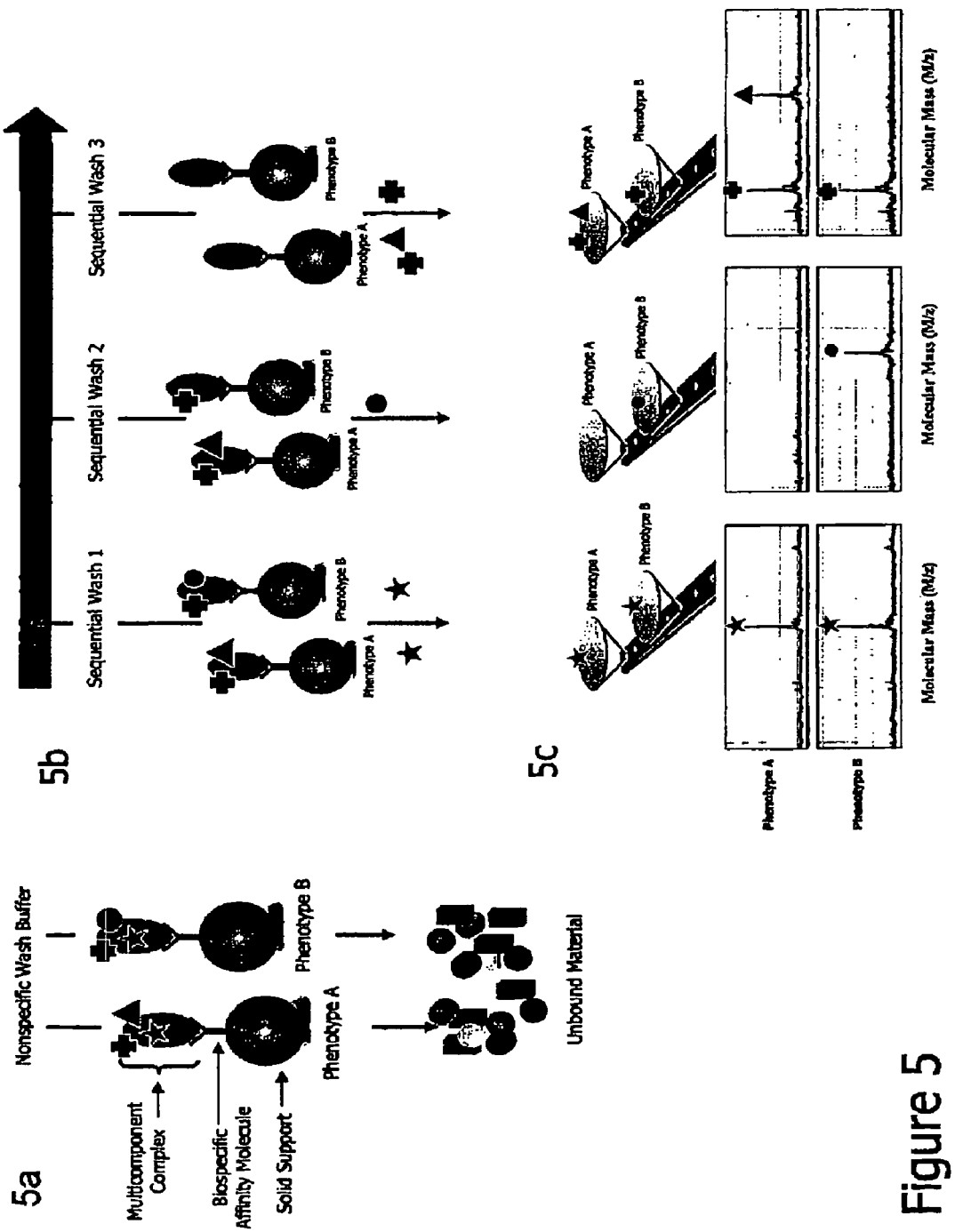
FIG. 5 depicts a method of using the method of FIG. 4 to create an expression interaction difference map of components between samples of different kinds. It shows one component being eluted in different washes between the samples.
Figure 6:
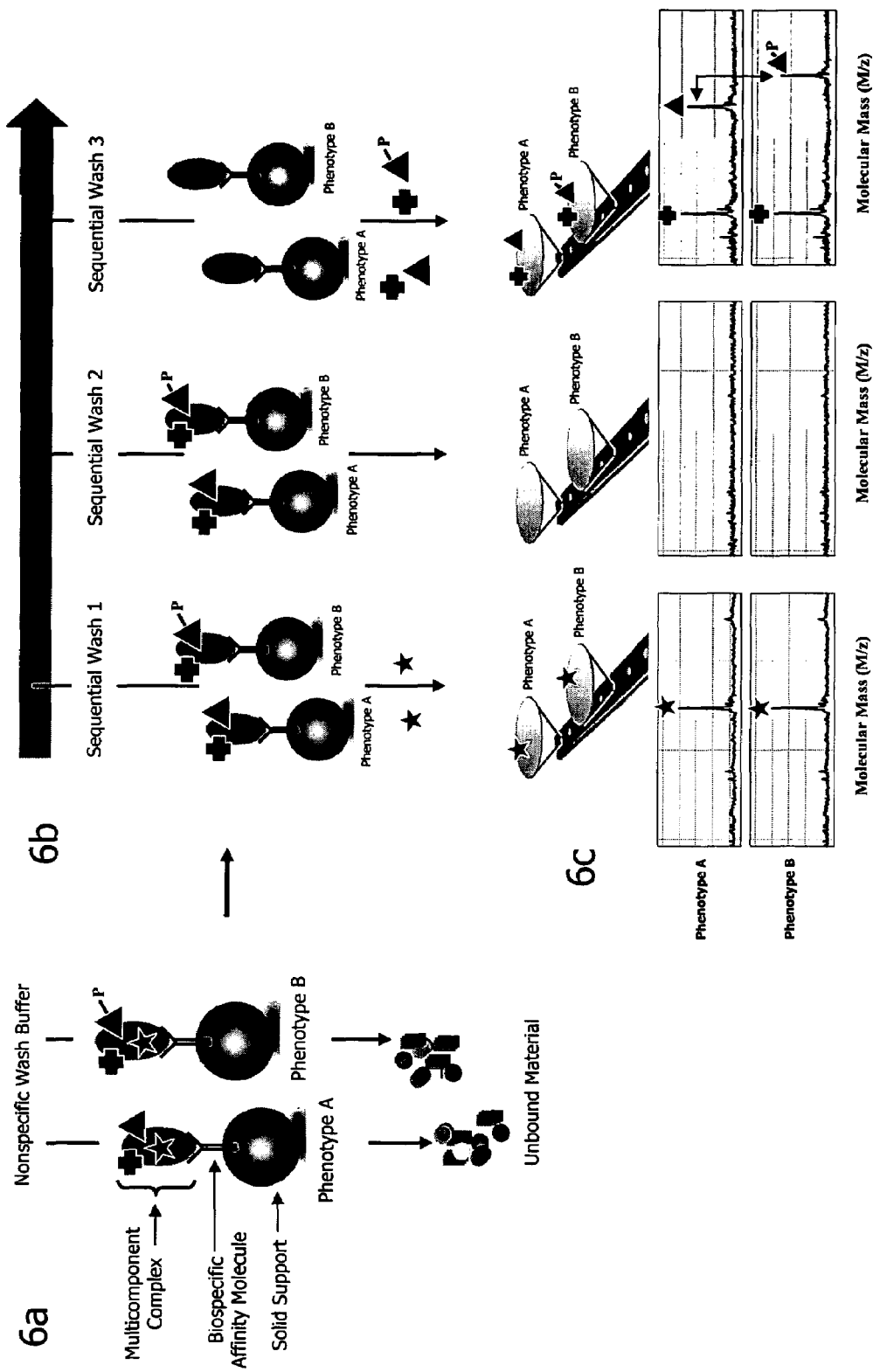
FIG. 6 depicts a method of using the method of FIG. 4 to create an expression interaction difference map of components between samples of different kinds. It shows one component being eluted in the same wash between the samples, but exhibiting a different mass due to alteration in one of the samples.

Referring to FIG. 5, step 5a (and FIG. 6, step 6a), a multicomponent complex from a plurality of different samples are immobilized on solid supports (e.g., physically separated). The samples may differ according to any phenotypic trait of interest. However, useful biological characteristics (e.g., phenotypic traits) include pathological condition v. non-pathological condition (e.g., cancer v. non-cancer), drug responder v. drug non-responder, toxic response v. non-toxic response and progressor to disease state v. non-progressor to disease state. Samples may be derived by natural means, such as those associated with normal genetic variation (species variation, race variation, gender variation, diet variation, etc) or samples may be generated by manipulation of a biological system, such as gene knockout, siRNA-induced transcription inhibition or treatment with organic or inorganic compounds that induce phenotypic changes.

In another embodiment, the samples to be compared are exposed to different conditions. For example, one sample may be a cell or an in vitro translation system, which is exposed to an inhibitory nucleic acid, such as anti-sense RNA, a ribozyme or RNAi, which inhibits the expression of a particular mRNA. The other sample may be from the same type of cell or in vitro translation system, but which has not been exposed to the inhibitory nucleic acid.

The plurality of samples can be as few as two (e.g., one pathological sample and one non-pathological sample). However, for purposes of creating clinically useful information, many samples of each class of sample must be used. For example, one might use at least 10, at least 100 or at least 1000 samples from each class.

Each sample is analyzed for component interaction as described above. This is depicted in FIG. 5, steps 5b and 5c (and FIG. 6, steps 6b and 6c). Upon comparison of the data from the different classes, different types of interactions may be detected. For example, depicted in the last pair of panels of FIG. 5, step 5c, one may find that a particular component elutes under different stringency in the two samples. This indicates that the character of the interaction between components in the different samples is different. Alternatively, as depicted in the last panel of FIG. 6, step 6c, one may determine that the component elutes in the same elution wash in the different samples, but has a different mass. This may indicate that the component has been differently modified between the two samples, for example by being post translationally modified (e.g, phosphorylated, glycosylated, acylated, biotinylated and cleavage) in one but not the other.

Patterns of difference in interaction between components may be useful to classify an unknown sample into one or another class, for example, as pathological or non-pathological. Such classification is useful for clinical purposes, for example diagnostic purposes. For these purposes, it is useful to profile, in each sample, a plurality of different components of a plurality of different complexes. The data matrices resulting from these profiles can be used to train a learning algorithm as described above to produce a classification algorithm to classify an unknown sample into either of the classes. For example, an unknown sample from a subject being tested for cancer can be profiled for component interaction, and this profile can be submitted to the classification algorithm for this cancer. The classification algorithm will qualify the subject as having cancer or not having cancer based on the pattern of interactions determined in the sample.

This invention also contemplates a second method of generating an interaction profile. According to this second method a multicomponent biological complex is again immobilized on a solid support through a biospecific affinity reagent that specifically binds one component of the complex. However, rather than washing the same solid support with a series of washes, in this embodiment, the solid supports are divided into a plurality of aliquots, and each aliquot is washed with a different one of the series of elution washes. Of course, one could divide a single batch of equilibrated solid supports into the plurality of aliquots, or one could produce a plurality of aliquots separately. The significant thing is to provide a plurality of aliquots comprising the complex immobilized to the solid supports that can be subject to independent washing.

Figure 7:
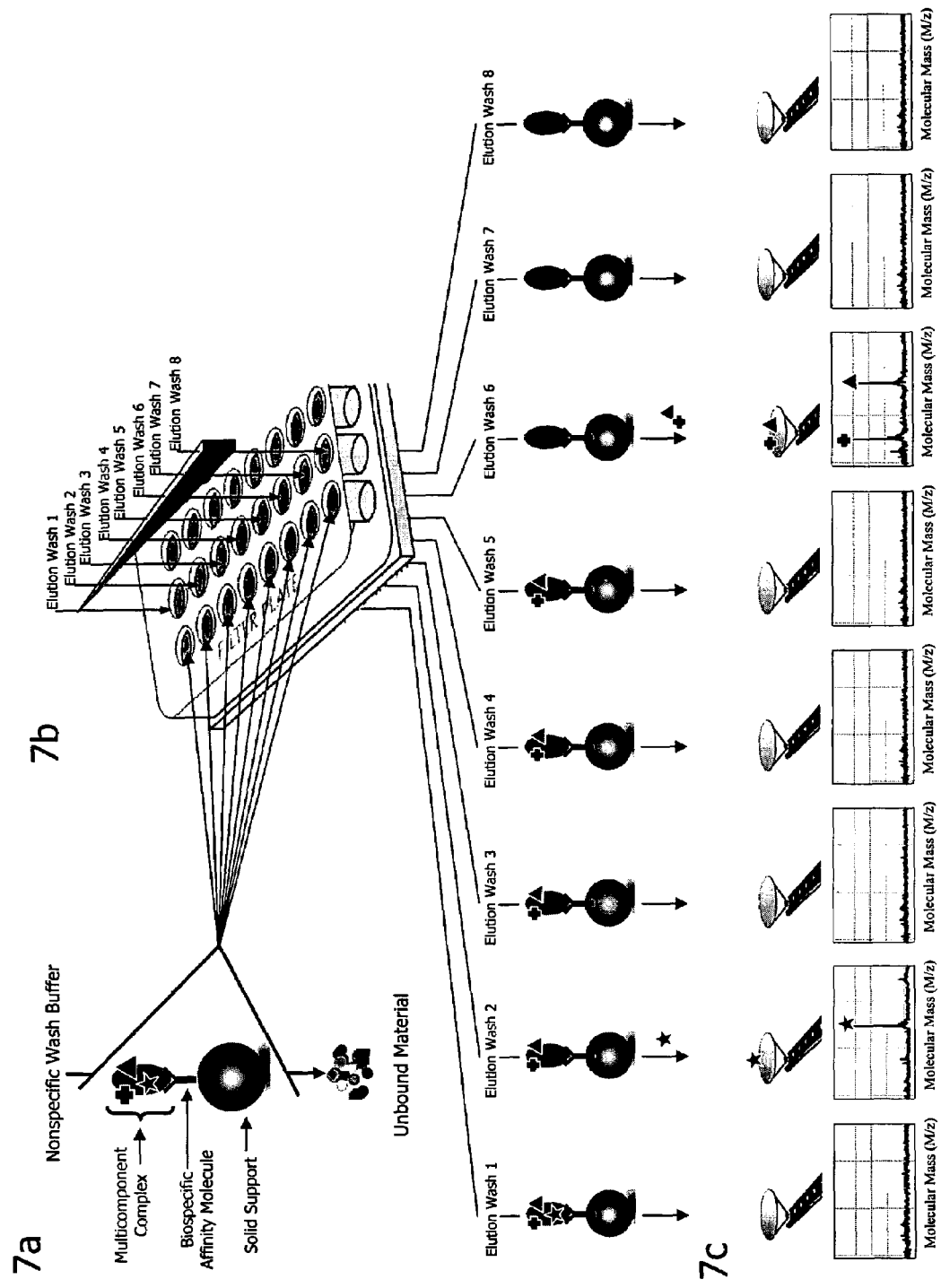
FIG. 7 depicts a method of using a series of elution washes that form a gradient on different aliquots containing the same immobilized multicomponent biological complex to map interaction between components.

The method is depicted in FIG. 7. FIG. 7, step 7a shows the capture of complex on a solid support and the removal of unbound material. In step 7b the solid support is divided into a plurality (here, eight) aliquots, and placed in different wells of a multiwell microtiter drip plate. Each well is now washed with one of a series of eight different elution washes forming a gradient, depicted by the wedge of increasing width. This produces eight elution washes that may or may not contain a component that has been eluted from the complex. The contents of each elution wash are then detected. (See FIG. 7, step 7c.)

Figure 8:
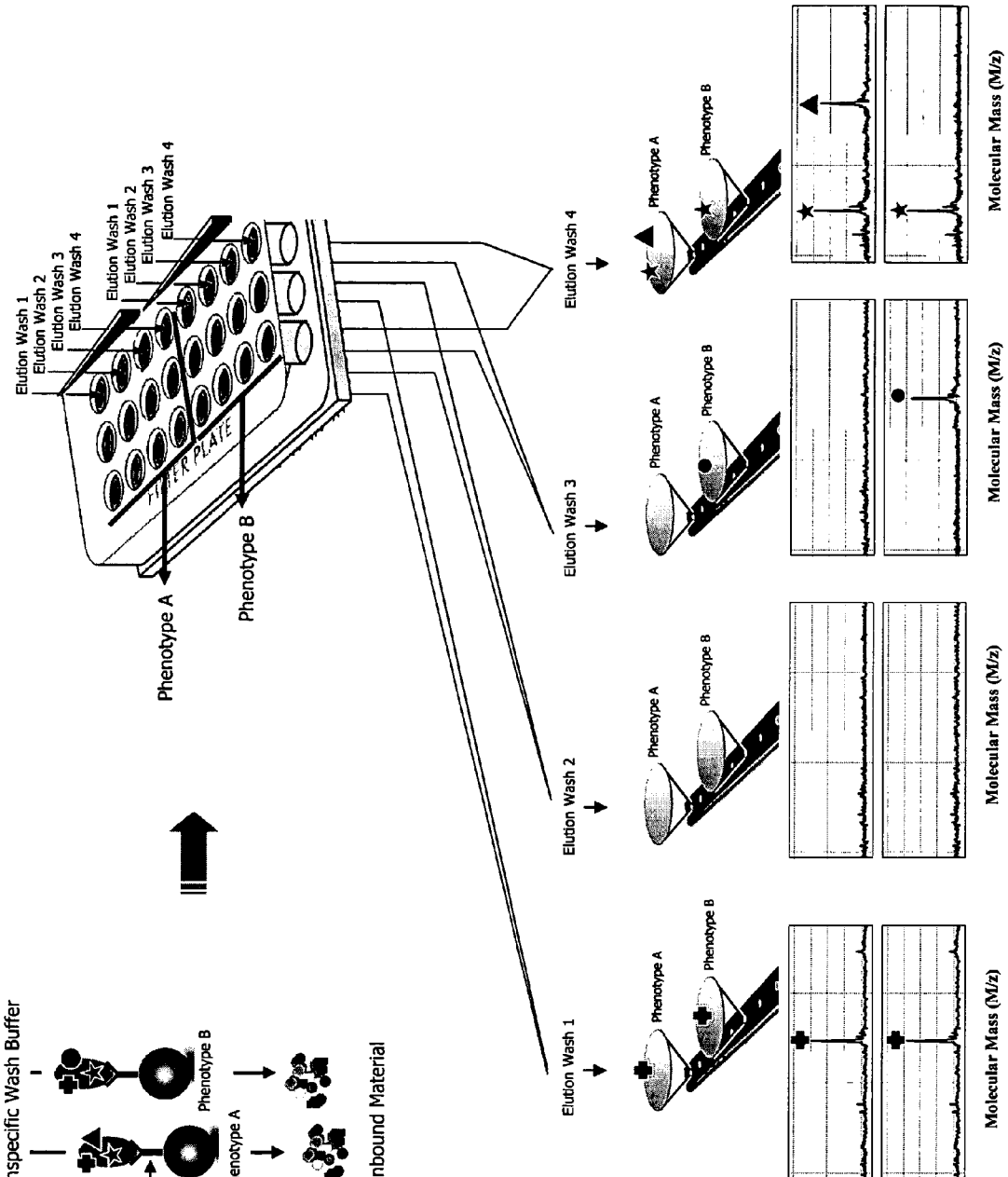
FIG. 8 depicts a method of using the method of FIG. 7 to create an expression interaction difference map of components between samples of different kinds. It shows one component being eluted in different washes between the samples.
Figure 9:
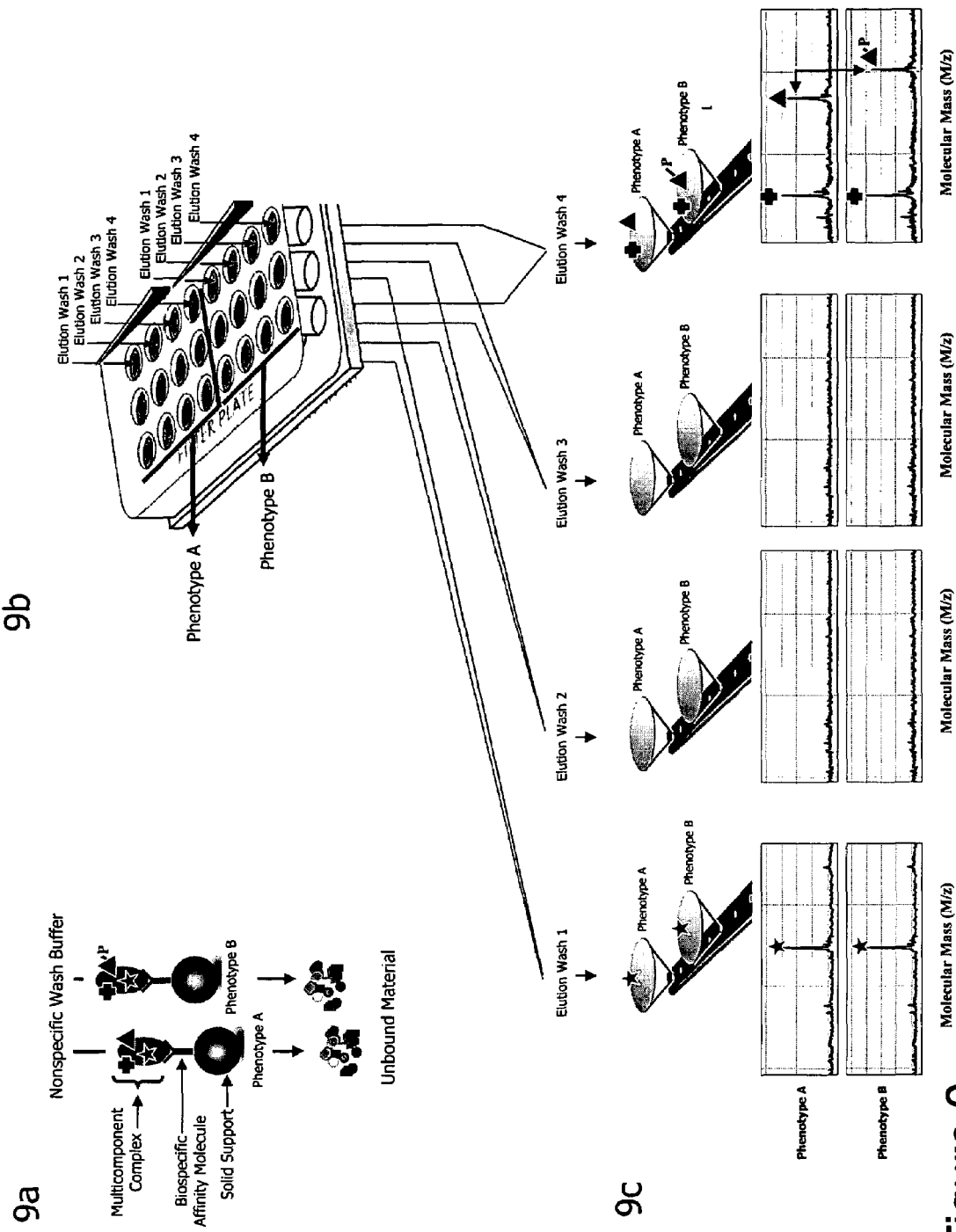
FIG. 9 depicts a method of using the method of FIG. 7 to create an expression interaction difference map of components between samples of different kinds. It shows one component being eluted in the same wash between the samples, but exhibiting a different mass due to alteration in one of the samples.

The method of this embodiment also can be used to detect differences in component interaction between samples, using techniques as described in the first method. These methods are depicted in FIGS. 8 and 9.

In this example, a complex from a sample of phenotype A and phenotype B are captured on solid supports. (See FIG. 8, step 8a and FIG. 9, step 9a). Each is divided into four aliquots and each aliquot is added to a different well of a microtiter plate. (See FIG. 8, step 8b and FIG. 9, step 9b). The four aliquots of each phenotype are washed with one buffer is a gradient series (Elution washes 1-4 in FIG. 8, step 8b and FIG. 9, step 9b). The components in the elution washes are detected. (FIG. 8, step 8c and FIG. 9, step 9c). Again, this may show that one component is eluted in a different wash (FIG. 8, step 8c) or in the same wash, but having a different molecular mass (FIG. 9, step 9c).

Again, the parameters of these methods can be varied. For example, one could perform this method on a plurality of different samples exhibiting phenotype A and a plurality of different samples exhibiting phenotype B. One could divide the solid supports into a plurality of sets of aliquots, and wash each set with gradient washes involving different solutes, for example, wash a first set of aliquots with a pH gradient, a second set of aliquots with a salt gradient and a third set of aliquots with a detergent gradient.

II. Binding Multicomponent Biological Complexes or Their Components with Affinity Molecules Multicomponent biological complexes are commonly found in complex mixtures containing a diverse population of biomolecules. In order to analyze the quaternary structure of a multicomponent biological complex and the interaction of its components, the complex must first be isolated from any such contaminants that are capable of interfering with the analysis. This is most conveniently accomplished using affinity or "bait" molecules that specifically bind one or more components of the multicomponent biological complex of interest. Suitable affinity molecules include antibodies directed to one or more antigenic components present in the complex, receptors, enzymes, and in the cases where the multicomponent biological complex itself is an enzyme, substrates for the activity associated with the multicomponent biological complex. Affinity molecules can be modified to enhance their binding and retention to the multicomponent biological complex. For example, substrates can be chemically modified to slow or prevent their conversion to product by the multicomponent biological complex-associated enzyme.

The multicomponent biological complex can be bound to affinity molecules of the present invention that are either free in solution or bound to a solid support. Binding between a multicomponent biological complex and an affinity molecule free in solution is typically followed by immobilizing the affinity molecule to a solid support as the first step in isolating and analyzing the multicomponent biological complex.

Suitable biological sources for recovering multicomponent biological complexes to be studied using the present invention include, e.g., extracts from biological samples, such as tissue lysates, cell lysates, body fluids or, in vitro translation systems. Preferably, the sample is in liquid form and obtained from cell lysates from specific tissues, organs or organisms.

III. Immobilizing Affinity Molecules on a Solid Support

As noted above, the multicomponent biological complex of interest can be isolated by first binding an affinity molecule to the complex followed by immobilizing the affinity molecule on a solid support. Alternatively, the affinity molecule can first be immobilized on a solid support and then the multicomponent biological complex bound to the immobilized affinity molecule. Any suitable method that will enable binding between the multicomponent biological complex and the affinity molecule can be used. E.g., the affinity molecule can simply be mixed or combined with the sample.

Any suitable method can also be used to immobilize the affinity molecule to the solid support, e.g., bathing, soaking, dipping, spraying, washing over, or pipetting, etc. Generally, a volume of sample containing from a few attomoles to 100 picomoles in about 1 µl to 500 µl is sufficient for binding to the support. The sample should contact the affinity molecule for a period of time sufficient to allow the multicomponent biological complex to bind. Typically, the sample and the affinity molecule are contacted for a period of between about 30 seconds and about 12 hours, and preferably, between about 30 seconds and about 15 minutes. Typically, the sample is contacted to the affinity molecule under ambient temperature and pressure conditions. For some samples, however, modified temperature (typically 4° C. through 37°

C.) and pressure conditions can be desirable, which conditions are determinable by those skilled in the art.

In addition, the sample can be contacted to the support or the free affinity molecule by solubilizing the sample in or mixing the sample with an eluant and contacting the solution of eluant and sample to the support or the free affinity molecule using any of the foregoing techniques. Exposing the sample to an eluant prior to binding the multicomponent biological complex to the affinity molecule has the effect of modifying the selectivity of the affinity molecule while simultaneously contacting it with the sample. Those components of the sample that will bind to the affinity molecule and thereby be retained will include only those components which will bind the affinity molecule in the presence of the particular eluant which has been combined with the sample, rather than all components which will bind to the affinity molecule in the absence of elution characteristics which modify the selectivity of the affinity molecule.

The sample should be contacted to the affinity molecule for a period of time sufficient to allow the complex of interest to bind. Typically, the sample is contacted with the affinity molecule for a period of between about 30 seconds and about 12 hours. Preferably, the sample is contacted to the affinity molecule for a period of between about 30 seconds and about 15 minutes.

The temperature at which the sample is contacted to the affinity molecule is a function of the particular sample and affinity molecule selected. Typically, contact is made under ambient temperature and pressure conditions, however, for some samples, modified temperature (typically 4° C. through 37° C.) and pressure conditions can be desirable and will be readily determinable by those skilled in the art.

The affinity molecule is bound to a solid support, capable of immobilizing the multicomponent biological complex while leaving the remaining components of the biological sample free and available for removal by a wash step(s), as described below. The solid support can be any surface that is insoluble, or capable of being rendered insoluble, in the biological sample containing the multicomponent biological complex being immobilized. For example, one embodiment utilizes an affinity molecule bound to a predominantly planar surface. More preferably, the affinity molecule is bound to a microparticle or bead. Still other embodiments utilize solid supports with particular physical properties allowing the support and any associated capture reagent/analyte to be isolated from the biological sample. For example, magnetic microparticles derivatized with specific antibodies can be used. A slurry of derivatized magnetic microparticles can be made from the biological sample. The beads and multicomponent biological complex can then be isolated with a magnet. The solid support can also be a SELDI-MS probe with affinity surfaces, each comprising affinity molecules specifically recognizing a multicomponent biological complex of interest. Each solid support used in the invention can immobilize a different affinity molecule capable of recognizing a different multicomponent biological complex.

IV. Washing Bound Multicomponent Complexes to Differentially Elute Components

Multicomponent biological complexes of interest can consist of any association of biomolecules as described previously in this application. Interaction between the components of the multicomponent biological complex can be of any type including covalent, ionic, hydrophobic, allosteric and coordinate binding, as occurs in chelation complexes. Examples of components that may be found in multicomponent biological complexes of interest include, but are not limited to, peptides, proteins, nucleic acids, carbohydrates, polysaccharides and fragments of biological macromolecules set forth above, such as nucleic acid fragments, peptide fragments, and protein fragments. Multicomponent biological complexes of interest will frequently be heterogeneous in nature, including protein-DNA complexes, receptor-ligand complexes, and enzyme-substrate complexes.

A. Wash Solutions

In order to remove contaminants frequently found in samples containing multicomponent biological complexes, the immobilized multicomponent biological complex of interest should be treated with an initial mild wash solution prior to any selective elution designed for analytical purposes. Typically an initial wash solution will be at a physiologic pH and ionic strength and the wash will be conducted under ambient conditions of temperature and pressure. Under certain circumstances, e.g., when the components of the multicomponent biological complex of interest are still immobilized after an elution wash that is of a particular stringency has been carried out, the stringent wash may be the only wash step performed. When it is anticipated that the multicomponent biological complex components of interest will remain associated with the affinity molecule immobilized to the solid support after the most stringent wash, then the solid support used is preferably an MS probe, most preferably a SELDI MS probe, with an adsorbent surface comprising the affinity molecule specifically binding the multicomponent biological complex.

B. Modifying Wash Solution Characteristics and Formulating Elution Wash Solutions After removal of unbound components from the solid supports, the supports are washed with a series of washes that form a gradient of increasing or decreasing strength based on an increasing or decreasing concentration of a particular solute in the solution. Accordingly, each subsequent wash solution increases in stringency, with weaker solutions stripping off weakly bound components and stronger solutions stripping of more tightly bound components. By exposing the bound complex to a series of washes, each subsequent wash being more stringent than the previous wash, components can be washed off sequentially from most weakly bound to most tightly bound.

In general, wash solutions selectively modify the threshold of absorption between the multicomponent biological complex and the affinity molecule. The ability of an eluant to desorb and elute a bound component of the multicomponent biological complex is a function of its elution characteristics. Different eluants can exhibit grossly different elution characteristics, somewhat different elution characteristics, or subtly different elution characteristics.

An important aspect of the present invention is the formulation of wash solutions used initially to remove contaminants from the immobilized multicomponent biological complexes of interest and secondly to differentially elute components from the immobilized complex for analysis. Moreover, it is the character of the elution wash solutions eluting particular complexes that illuminates which types of biomolecular interactions are important in associating the eluted component to the multicomponent biological complex. This section outlines several ways in which the wash solutions of the present invention can be modified to effect efficient initial washes and subsequently to induce component elution from the multicomponent biological complex.

To increase the wash stringency of the wash solution, buffers and other additives can be incorporated into the wash solution. The variety of wash solutions used to elute molecules from an affinity chromatography surface is well known in the art. Wash solutions include, but are not limited to, pH-based eluants (e.g., acids and bases), ionic strength-based eluants (e.g., a salt), water structure-based eluant (e.g., urea or a chaotropic salt solution (e.g., sodium thiocyanate)), detergent-based eluants (e.g., CHAPS, TWEEN, SDS and NP-40), hydrophobicity-based eluants (e.g., organic solvents, thiophilic salts and acetonitrile), biomolecule-based eluants (e.g., an amino acid, a nucleotide, a simple sugar, a fatty acid and polymers of these) and binding competitor eluants. Binding competitor eluants include as a solute a molecule that competes with a component for binding to another component. The binding competitor could be, for example, a small organic molecule, such as a drug candidate.

The selection of a particular wash solution or additive is dependent on experimental conditions (e.g., types of affinity molecules used or multicomponent biological complex to be detected), and can be determined by those of skill in the art.

Suitable washes can be selected from any of the foregoing categories or can be combinations of two or more of the foregoing washes. Washes that comprise two or more of the foregoing washes are capable of modifying the selectivity of the affinity molecule for the multicomponent biological complex on the basis of multiple elution characteristics.

C. Variability of Two Parameters

The ability to provide different binding characteristics by selecting different affinity molecules and the ability to provide different elution characteristics by washing with different washes permits variance of two distinct parameters each of which is capable of individually effecting the selectivity with which multicomponent biological complexes are bound to the affinity molecule. The fact that these two parameters can be varied widely assures a broad range of binding attraction so that the methods of the present invention can be useful for binding and thus detecting many different types of multicomponent biological complexes.

The selection of affinity molecules and washes for use in analyzing a particular sample will depend on the nature of the sample, and the particular multicomponent biological complex or class of multicomponent biological complexes to be characterized, even if the nature of the multicomponent biological complex(es) is not known. Typically, it is advantageous to provide a system exhibiting a wide variety of binding characteristics and a wide variety of elution characteristics, particularly when the composition of the sample to be analyzed is unknown. By providing a system exhibiting broad ranges of selectivity characteristics, the likelihood that the multicomponent biological complex of interest will be retained by one or more of the affinity molecules is significantly increased.

One skilled in the art of chemical or biochemical analysis is capable of determining the selectivity conditions useful for retaining a particular multicomponent biological complex by providing a system exhibiting a broad range of binding and elution characteristics and observing binding and elution characteristics which provide the best resolution of the multicomponent biological complex.

Because the present invention provides for systems including broad ranges of selectivity conditions, the determination by one skilled in the art of the optimum binding and elution characteristics for a given multicomponent biological complex easily accomplished without the need for undue experimentation.

D. Washing the Affinity Molecule with Wash Solutions

After the sample containing the multicomponent biological complex is contacted with the affinity molecule and the affinity molecule is immobilized to the solid support, the multicomponent biological complex can be washed with an initial wash solution and any number of elution wash solutions of the present invention. Typically, to provide a multidimensional analysis, each affinity molecule location is washed with at least the initial wash solution to remove contaminants from the sample and one elution wash solution. Washing the multicomponent biological complex typically modifies the complex component population retained on a specified affinity molecule. The combination of the binding characteristics of the component of the complex and the elution characteristics of the elution wash solutions provide the selectivity conditions that control which components are retained associated with the solid support via the affinity molecule after elution washing. Thus, the washing step selectively removes components from the multicomponent biological complex.

The washing step can be carried out using a variety of techniques. For example, as seen above, the sample can be solubilized in or admixed with the first wash prior to contacting the sample to the affinity molecule. Exposing the sample to the initial wash solution prior to or simultaneously with contacting the sample to the affinity molecule has the same net effect as binding the multicomponent biological complex to the affinity molecule and subsequently washing the affinity molecule with the initial wash solution. After the multicomponent biological complex is bound to the affinity molecule, the complex can be washed with one or more elution wash solutions.

Washing an affinity molecule having the multicomponent biological complex bound thereto can be accomplished by bathing, soaking, or dipping the substrate having the affinity molecule and multicomponent biological complex bound thereon in an wash; or by rinsing, spraying, or washing over the substrate with the wash.

The foregoing method is also useful when affinity molecules are provided at a plurality of predetermined addressable locations, whether the affinity molecules are all the same or different. However, when the multicomponent biological complex is bound to affinity molecules at a plurality of locations, the washing step may alternatively be carried out using a more systematic and efficient approach. Namely, the step of washing can be carried out by washing an affinity molecule at a first location with wash, then washing a second affinity molecule with wash, then desorbing and detecting the multicomponent biological complex components retained by the first affinity molecule and thereafter desorbing and detecting multicomponent biological complex retained by the second affinity molecule. In other words, all of the affinity molecules are exposed to the initial wash together and thereafter, multicomponent biological complex components released from each affinity molecule location can be individually analyzed. If desired, after detection of the multicomponent biological complex components released from each affinity molecule location, a second stage of elution washes for each affinity molecule location may be conducted followed by a second stage of detection and/or analysis. The steps of washing all affinity molecule locations, followed by desorption and detection of released components for each affinity molecule location can be repeated for a plurality of different elution washes. In this manner, an entire array may be utilized to efficiently determine the character of multicomponent biological complexes in a sample.

Using the methods of the present invention, it is possible to collect data regarding the binding properties of any given component of a multicomponent biological complex based on the elution properties of the elution wash solutions used to extract the complex.

V. Adsorbing Eluted Components on SELDI MS Probes

In order to generate interaction difference maps using the methods of the present invention, components of the multicomponent biological complex to be analyzed may be adsorbed to an MS probe of the present invention. Typically SELDI-MS probes are used for this purpose because of the desirable characteristics they possess, the principle one being multiple addressable adsorbent locations for binding biomolecules. SELDI-MS probes, unlike their MALDI predecessors, can comprise a plurality of adsorbents on a single probe. This multiplex format allows highly refined efficient analysis of samples in a high throughput setting as described above. The different adsorbents used with SELDI-MS probes can exhibit grossly different binding characteristics, somewhat different binding characteristics, or subtly different binding characteristics.

Adsorbents that exhibit grossly different binding characteristics typically differ in their bases of attraction or mode of interaction. The basis of attraction is generally a function of chemical or biological molecular recognition. Bases for attraction between an adsorbent and a biomolecule include, for example, (1) a salt-promoted interaction, e.g., hydrophobic interactions thiophilic interactions, and immobilized dye interactions; (2) hydrogen bonding and/or van der Waals forces interactions and charge transfer interactions, such as in the case of a hydrophilic interactions; (3) electrostatic interactions, such as an ionic charge interaction, particularly positive or negative ionic charge interactions; (4) the ability of the analyte to form coordinate covalent bonds (i.e., coordination complex formation) with a metal ion on the adsorbent; (5) enzyme-active site binding; (6) reversible covalent interactions, for example, disulfide exchange interactions; (6) glycoprotein interactions; (7) biospecific interactions; or (8) combinations of two or more of the foregoing modes of interaction. That is, the adsorbent can exhibit two or more bases of attraction, and thus be known as a "mixed functionality" adsorbent. Typical adsorbent chemistries used in conjunction with SELDI-MS probes are discussed below.

A. Salt-promoted Interaction Adsorbents

Adsorbents that are useful for observing salt-promoted interactions include hydrophobic interaction adsorbents. Examples of hydrophobic interaction adsorbents include matrices having aliphatic hydrocarbons, specifically $C_1$-$C_{18}$ aliphatic hydrocarbons; and matrices having aromatic hydrocarbon functional groups such as phenyl groups. Hydrophobic interaction adsorbents bind analytes that include uncharged solvent exposed amino acid residues, and specifically amino acid residues, which are commonly referred to as nonpolar, aromatic and hydrophobic amino acid residues, such as phenylalanine and tryptophan. Specific examples of analytes that will bind to a hydrophobic interaction adsorbent include lysozyme and DNA. Without wishing to be bound by a particular theory, it is believed that DNA binds to hydrophobic interaction adsorbents by the aromatic nucleotides in DNA, specifically, the pyridine and pyrimidine groups.

Another adsorbent useful for observing salt-promoted interactions includes thiophilic interaction adsorbents, such as for example T-GEL™, which is one type of thiophilic adsorbent commercially available from Pierce, Rockford, Ill. Thiophilic interaction adsorbents bind, for example, immunoglobulins, such as IgG.

A third adsorbent for observing salt-promoted interactions includes immobilized dye interaction adsorbents. Immobilized dye interaction adsorbents include matrices of immobilized dyes such as for example CIBACHRON™ blue available from Pharmacia/Amicon. Immobilized dye interaction adsorbents bind proteins and DNA generally. One specific example of a protein that binds to an immobilized dye interaction adsorbent is bovine serum albumin (BSA).

B. Hydrophilic Interaction Adsorbents

Adsorbents that are useful for observing hydrogen bonding and/or van der Waals forces on the basis of hydrophilic interactions include surfaces comprising normal phase adsorbents such as silicon-oxide (i.e., glass). The normal phase or silicon-oxide surface, acts as a functional group. In addition, adsorbents comprising surfaces modified with hydrophilic polymers such as polyethylene glycol, dextran, agarose, or cellulose can also function as hydrophilic interaction adsorbents. Most proteins will bind hydrophilic interaction adsorbents because of a group or combination of amino acid residues that bind through hydrophilic interactions involving hydrogen bonding or van der Waals forces.

C. Electrostatic Interaction Adsorbents

Adsorbents that are useful for observing electrostatic or ionic charge interactions include anionic adsorbents such as, for example, matrices of sulfate anions (i.e., $SO_3^-$) and matrices of carboxylate anions (i.e., $COO^-$) or phosphate anions ($—OPO_3—$). Matrices having sulfate anions are permanent negatively charged. However, matrices having carboxylate anions have a negative charge only at a pH above their pKa. At a pH below the pKa, the matrices exhibit a substantially neutral charge. Suitable anionic adsorbents also include anionic adsorbents which are matrices having a combination of sulfate and carboxylate anions and phosphate anions. The combination provides an intensity of negative charge that can be continuously varied as a function of pH. These adsorbents attract and bind proteins and macromolecules having positive charges, such as for example ribonuclease and myoglobin. Without wishing to be bound by a particular theory, it is believed that the electrostatic interaction between an adsorbent and positively charged amino acid residues including lysine residues, arginine residues, and histidyl residues are responsible for the binding interaction.

Other adsorbents that are useful for observing electrostatic or ionic charge interactions include cationic adsorbents. Specific examples of cationic adsorbents include matrices of secondary, tertiary or quaternary amines. Quaternary amines are permanently positively charged under the conditions for adsorption. However, secondary and tertiary amines have charges that are pH dependent. At a pH below the pKa, secondary and tertiary amines are positively charged, and at a pH above their pKa, they are negatively charged. Suitable cationic adsorbents also include cationic adsorbents which are matrices having combinations of different secondary, tertiary, and quaternary amines. The combination provides an intensity of positive charge that can be continuously varied as a function of pH. Cationic interaction adsorbents bind anionic sites on molecules including proteins having solvent exposed amino acid residues, such as aspartic acid and glutamic acid residues.

In the case of ionic interaction adsorbents (both anionic and cationic) it is often desirable to use a mixed mode ionic adsorbent containing both anions and cations. Such adsorbents provide a continuous buffering capacity as a function of pH. The continuous buffering capacity enables the exposure of a combination of analytes to eluants having differing buffering components especially in the pH range of from 2 to 11. This results in the generation of local pH environments on the adsorbent that are defined by immobilized titratable proton exchange groups. Such systems are equivalent to the solid phase separation technique known as chromatofocusing.

Still other adsorbents that are useful for observing electrostatic interactions include dipole-dipole interaction adsorbents in which the interactions are electrostatic but no formal charge or titratable protein donor or acceptor is involved.

D. Coordinate Covalent Interaction Adsorbents

Adsorbents that are useful for observing the ability to form coordinate covalent bonds with metal ions include matrices bearing, for example, divalent and trivalent metal ions. Matrices of immobilized metal ion chelators provide immobilized synthetic organic molecules that have one or more electron donor groups, which form the basis of coordinate covalent interactions with transition metal ions. The primary electron donor groups functioning as immobilized metal ion chelators include oxygen, nitrogen, and sulfur. The metal ions are bound to the immobilized metal ion chelators resulting in a metal ion complex having some number of remaining sites for interaction with electron donor groups on the analyte. Suitable metal ions include in general transition metal ions such as copper, nickel, cobalt, zinc, iron, and other metal ions such as Al, Ca. Without wishing to be bound by any particular theory, metals ions are believed to interact selectively with specific amino acid residues in peptides, proteins, or nucleic acids. Typically, the amino acid residues involved in such interactions include histidine residues, tyrosine residues, tryptophan residues, cysteine residues, and amino acid residues having oxygen groups such as aspartic acid and glutamic acid. For example, immobilized ferric ions interact with phosphoserine, phosphotyrosine, and phosphothreonine residues on proteins. Depending on the immobilized metal ion, only those proteins with sufficient local densities of the foregoing amino acid residues will be retained by the adsorbent. Some interactions between metal ions and proteins can be so strong that the protein cannot be severed from the complex by conventional means.

E. Enzyme-Active Site Interaction Adsorbents

Adsorbents that are useful for observing enzyme-active site binding interactions include proteases (such as trypsin), phosphatases, kinases, and nucleases. The interaction is a sequence-specific interaction of the enzyme binding site on the analyte (typically a biopolymer) with the catalytic binding site on the enzyme. Enzyme binding sites of this type include, for example, active sites of trypsin interacting with proteins and peptides having lysine-lysine or lysine-arginine pairs in their sequence. More specifically, soybean trypsin inhibitor interacts with and binds to an adsorbent of immobilized trypsin.

F. Reversible Covalent Interaction Adsorbents

Adsorbents that are useful for observing reversible covalent interactions include disulfide exchange interaction adsorbents. Disulfide exchange interaction adsorbents include adsorbents comprising immobilized sulfhydryl groups, e.g., mercaptoethanol or immobilized dithiothrietol. The interaction is based upon the formation of covalent disulfide bonds between the adsorbent and solvent exposed cysteine residues on the analyte. Such adsorbents bind proteins or peptides having cysteine residues and nucleic acids including bases modified to contain reduced sulfur compounds.

G. Glycoprotein Interaction Adsorbents

Adsorbents that are useful for observing glycoprotein interactions include glycoprotein interaction adsorbents, which include adsorbents having immobilize lectins (i.e., proteins bearing oligosaccharides) therein, such as CON-CONAVALIN™, which is commercially available. Such adsorbents function on the basis of the interaction involving molecular recognition of carbohydrate moieties on macromolecules. Examples of analytes that interact with and bind to glycoprotein interaction adsorbents include glycoproteins, particularly histidine-rich glycoproteins, whole cells and isolated subcellular fractions.

H. Biospecific Interaction Adsorbents

Adsorbents that are useful for observing biospecific interactions are generically termed "biospecific affinity adsorbents." Examples of biospecific affinity adsorbents include any adsorbent that specifically interacts with and binds a particular biomolecule. Biospecific affinity adsorbents include for example, immobilized antibodies, immobilized single chain antibodies, immobilized specific binding fragments of an antibody; an immobilized affibody, immobilized DNA which binds to DNA binding proteins, DNA, and RNA; immobilized enzymes, immobilized substrates or inhibitors which bind to proteins and enzymes; immobilized drugs which bind to drug binding proteins; immobilized ligands which bind to receptors; immobilized receptors which bind to ligands; immobilized RNA which binds to DNA and RNA binding proteins; immobilized aptamers, immobilized avidin or streptavidin which bind biotin and biotinylated molecules; immobilized phospholipid membranes and vesicles which bind lipid-binding proteins. Biospecific interaction adsorbents rely on known specific interactions such as those described above. Other examples of biospecific interactions for which adsorbents can be utilized will be readily apparent to those skilled in the art and are contemplated by the present invention.

The MS probe used to capture eluted components, or where applicable to serve as a solid support for the washing steps of the invention, can be shaped so that it is adapted for use with various components of the mass spectrometer of the invention, such as inlet systems and detectors. For example, the probe can be adapted for mounting in a horizontally and/or vertically translatable carriage that horizontally and/or vertically moves the probe to a successive position. This allows components bound to different locations of the adsorbent surface to be analyzed without requiring repositioning of the probe by hand. Probes are commercially available and can be purchased (e.g., ProteinChip®, Ciphergen Biosystems, Fremont, Calif.). The probes may be constructed of a variety of materials. Probe materials should not react with sample components, nor should they release molecular species outside those comprising the sample and adsorbents located on their surface as a consequence of exposure to the ionization source of the mass spectrometer. Probe materials include, but are not limited to, insulating materials (e.g., glass such as silicon oxide, plastic, ceramic), semi-conducting materials (e.g., silicon wafers), or electrically conducting materials (e.g., metals, such as nickel, brass, steel, aluminum, gold, or electrically conductive polymers), organic polymers, biopolymers, or any combinations thereof. The probe material can also be solid or porous. Probe materials suitable for use in embodiments of the invention are also described in, e.g., U.S. Pat. No. 5,617,060 (Hutchens and Yip) and WO 98/59360 (Hutchens and Yip).

VI. Preparing Loaded SELDI-MS Probes and Analysis by Mass Spectrometry

A. Sample Preparation

Prior to MS-analysis, an MS-matrix material must be added to the adsorbent-bound sample on the MS probe. The MS matrix can assist absorption of energy from an ionization source, e.g., from a gas phase ion spectrometer, and can assist desorption of sample components from the probe surface. The MS-matrix can be any suitable material that allows ionization and vaporization of the molecules of interest bound to the adsorbent, and also absorbs some of the ionization source's energy, thereby preventing the ionization source from fragmenting the sample molecules being analyzed. The absorption spectrum of the matrix should overlap the frequency of the laser pulse being used. The matrix should retain stability while at the same time allowing deposition of ionization energy. The matrix also should not react (modify) with the samples to be analyzed and must not sublime away at a rate incompatible with the duration of the analysis. Finally, the matrix should have appropriate chemical properties that allow ionization of the sample material. Common MS-matrix materials include hydroxycinnamic acid (CHCA), sinapinic acid, gentisic acid, trans-3-indoleacrylic acid (IAA), and cinnamic, nicotinic and vanillic acids. See, e.g., U.S. Pat. No. 5,719,060 (Hutchens & Yip) for additional description of MS matrices.

The MS matrix can be added to the multicomponent biological complex components in any suitable manner. For example, an MS matrix is mixed with the sample, and the mixture is placed on the adsorbent surface. In another example, an MS matrix can be placed on the adsorbent surface prior to contacting the adsorbent surface with the sample. In another example, the sample can be placed on the adsorbent surface prior to contacting the adsorbent surface with an MS matrix. Then the components bound to the adsorbent surface are desorbed, ionized and detected as described in detail below.

Alternatively, the probe can be a SEND probe, in which a layer of energy absorbing molecules is attached to the probe surface. The probe can be a SEND probe, alone, or it can also comprise an adsorbent and function in both SEAC and SEND modes.

B. Desorption/Ionization and Detection

Multicomponent biological complex components bound on the adsorbent surface of the MS probe can be desorbed and ionized using mass spectrometry. Any suitable ionizing mass spectrometer, e.g., a gas phase ion spectrometer, can be used as long as it allows the different multicomponent biological complex components bound by the adsorbent to be resolved. In a typical mass spectrometer, an MS probe carrying the multicomponent biological complex components bound by the adsorbent is introduced into an inlet system of the mass spectrometer. The components are then desorbed by a desorption source such as a laser, fast atom bombardment, high energy plasma, electrospray ionization, thermospray ionization, liquid secondary ion MS, field desorption, etc. The generated desorbed, volatilized species consist of preformed ions or neutrals which are ionized as a direct consequence of the desorption event. Generated ions are collected by an ion optic assembly, and then a mass analyzer disperses and analyzes the passing ions. The ions exiting the mass analyzer are detected by a suitable detector. The detector then translates information of the detected ions into mass-to-charge ratios. Detection of the presence of multicomponent biological complex components will typically involve detection of signal intensity. Any of the parts of a mass spectrometer (e.g., a desorption source, a mass analyzer, a detector, etc.) can be combined with other suitable parts described herein or others known in the art in embodiments of the invention.

Preferably, a laser desorption time-of-flight mass spectrometer is used in embodiments of the invention. In laser desorption mass spectrometry, a probe adsorbent comprising multicomponent biological complex components is introduced into an inlet system. The pathway components are desorbed and ionized into the gas phase by laser from the ionization source. The ions generated are collected by an ion optic assembly, and then in a time-of-flight mass analyzer, ions are accelerated through a short high voltage field and let drift into a high vacuum chamber. At the far end of the high vacuum chamber, the accelerated ions strike a sensitive detector surface at a different time. Since the time-of-flight is a function of the mass of the ions, the elapsed time between ion formation and ion detector impact can be used to identify the presence or absence of pathway components of specific mass to charge ratio.

In another embodiment, an ion mobility spectrometer can be used to detect multicomponent biological complex components. The principle of ion mobility spectrometry is based on different mobility of ions. Specifically, ions of a sample produced by ionization move at different rates, due to their difference in, e.g., mass, charge, or shape, through a tube under the influence of an electric field. The ions (typically in the form of a current) are registered at the detector, which can then be used to identify pathway components in a sample. One advantage of ion mobility spectrometry is that it can operate at atmospheric pressure.

VII. Comparing Test Data to Control Data and Generating Difference Maps

Data generated by desorption and detection of multicomponent biological complex components in a test sample can be compared to a control data to determine if the multicomponent biological complex in the test sample is normal. A control data refers to data obtained from comparable samples from a normal cell or person, which or who is known to have no defects in the multicomponent biological complex. For each multicomponent biological complex component being analyzed, a control amount of the same component from a normal sample is determined. Preferably, the control amount of each component is determined based upon a significant number of samples taken from normal cells or persons so that it reflects variations of the amount of these components seen in the normal cell or population.

If the test amount of particular components is significantly increased or decreased compared to the control amount of the component, then this is a positive indication that the test sample has a defect in the corresponding multicomponent biological complex. For example, if the test amount of a multicomponent biological complex-related component is increased or decreased by at least 1.5 fold, 2 fold, 5 fold or 10 fold compared to the control amount, then this is an indication that the test sample has a defect in that multicomponent biological complex. In some circumstances, if defect is severe, certain components of the multicomponent biological complex may be undetectable.

VIII. Applications

Using the data analysis methods discussed above, the present invention allows detection of changes in the composition of any multicomponent biological complex, including subtle changes in binding affinity between complex components. Such changes in component binding and complex composition are frequently associated with disease states. Examples of changes in multicomponent biological complex compositions and component affinities associated with disease states include hemophilia, diabetes, and many forms of cancer.

By monitoring the properties of the elution wash solution that extract each released component from the multicomponent biological complex, the present invention also provides an elegant method for characterizing the intracomplex affinities between individual components within the multicomponent biological complex. This characterization is further enhanced by the use of SELDI-MS probes. SELDI-MS probes provide an array of different adsorbent chemistries that can provide further insight into the binding properties of individual multicomponent biological complex components by noting which SELDI-MS probe adsorbents bind which components and with what affinity.

DEFINITIONS

Unless defined otherwise, all technical and scientific terms used herein have the meaning commonly understood by a person skilled in the art to which this invention belongs. The following references provide one of skill with a general definition of many of the terms used in this invention: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991). As used herein, the following terms have the meanings ascribed to them unless specified otherwise.

"Gas phase ion spectrometer" refers to an apparatus that detects gas phase ions. Gas phase ion spectrometers include an ion source that supplies gas phase ions. Gas phase ion spectrometers include, for example, mass spectrometers, ion mobility spectrometers, and total ion current measuring devices. "Gas phase ion spectrometry" refers to the use of a gas phase ion spectrometer to detect gas phase ions.

"Mass spectrometer" refers to a gas phase ion spectrometer that measures a parameter that can be translated into mass-to-charge ratios of gas phase ions. Mass spectrometers generally include an ion source and a mass analyzer. Examples of mass spectrometers are time-of-flight, magnetic sector, quadrupole filter, ion trap, ion cyclotron resonance, electrostatic sector analyzer and hybrids of these. "Mass spectrometry" refers to the use of a mass spectrometer to detect gas phase ions.

"Laser desorption mass spectrometer" refers to a mass spectrometer that uses laser energy as a means to desorb, volatilize, and ionize an analyte.

"Tandem mass spectrometer" refers to any mass spectrometer that is capable of performing two successive stages of m/z-based discrimination or measurement of ions, including ions in an ion mixture. The phrase includes mass spectrometers having two mass analyzers that are capable of performing two successive stages of m/z-based discrimination or measurement of ions tandem-in-space. The phrase further includes mass spectrometers having a single mass analyzer that is capable of performing two successive stages of m/z-based discrimination or measurement of ions tandem-in-time. The phrase thus explicitly includes Qq-TOF mass spectrometers, ion trap mass spectrometers, ion trap-TOF mass spectrometers, TOF-TOF mass spectrometers, fourier transform ion cyclotron resonance mass spectrometers, electrostatic sector-magnetic sector mass spectrometers, and combinations thereof.

"Mass analyzer" refers to a sub-assembly of a mass spectrometer that comprises means for measuring a parameter that can be translated into mass-to-charge ratios of gas phase ions. In a time-of-flight mass spectrometer the mass analyzer comprises an ion optic assembly, a flight tube and an ion detector.

"Ion source" refers to a sub-assembly of a gas phase ion spectrometer that provides gas phase ions. In one embodiment, the ion source provides ions through a desorption/ionization process. Such embodiments generally comprise a probe interface that positionally engages a probe in an interrogatable relationship to a source of ionizing energy (e.g., a laser desorption/ionization source) and in concurrent communication at atmospheric or subatmospheric pressure with a detector of a gas phase ion spectrometer.

Forms of ionizing energy for desorbing/ionizing an analyte from a solid phase include, for example: (1) laser energy; (2) fast atoms (used in fast atom bombardment); (3) high energy particles generated via beta decay of radionuclides (used in plasma desorption); and (4) primary ions generating secondary ions (used in secondary ion mass spectrometry). The preferred form of ionizing energy for solid phase analytes is a laser (used in laser desorption/ionization), in particular, nitrogen lasers, Nd-Yag lasers and other pulsed laser sources. "Fluence" refers to the energy delivered per unit area of interrogated image. A high fluence source, such as a laser, will deliver about 1 mJ/mm$^2$ to 50 mJ/mm$^2$. Typically, a sample is placed on the surface of a probe, the probe is engaged with the probe interface and the probe surface is struck with the ionizing energy. The energy desorbs analyte molecules from the surface into the gas phase and ionizes them.

Other forms of ionizing energy for analytes include, for example: (1) electrons which ionize gas phase neutrals; (2) strong electric fields to induce ionization from gas phase, solid phase, or liquid phase neutrals; and (3) a source that applies a combination of ionization particles or electric fields with neutral chemicals to induce chemical ionization of solid phase, gas phase, and liquid phase neutrals.

"Probe" in the context of this invention refers to a device adapted to engage a probe interface of a gas phase ion spectrometer (e.g., a mass spectrometer) and to present an analyte to ionizing energy for ionization and introduction into a gas phase ion spectrometer, such as a mass spectrometer. A "probe" will generally comprise a solid substrate (either flexible or rigid) comprising a sample-presenting surface on which an analyte is presented to the source of ionizing energy. An "MS probe" is a probe for a mass spectrometer.

"Surface-Enhanced Affinity Capture" ("SEAC") or "affinity capture mass spectrometry" is a version of SELDI that involves the use of probes comprising an absorbent surface (a "SEAC probe" or an "affinity capture probe"). "Adsorbent surface" refers to a surface to which is bound an adsorbent (also called a "capture reagent" or an "affinity reagent"). An adsorbent is any material capable of binding an analyte (e.g., a target polypeptide or nucleic acid). "Chromatographic adsorbent" refers to a material typically used in chromatography. Chromatographic adsorbents include, for example, ion exchange materials, metal chelators (e.g., nitriloacetic acid or iminodiacetic acid), immobilized metal chelates, hydrophobic interaction adsorbents, hydrophilic interaction adsorbents, dyes, simple biomolecules (e.g., nucleotides, amino acids, simple sugars and fatty acids) and mixed mode adsorbents (e.g., hydrophobic attraction/electrostatic repulsion adsorbents). "Biospecific adsorbent" refers to an adsorbent comprising a biomolecule, e.g., a nucleic acid molecule (e.g., an aptamer), a polypeptide, a polysaccharide, a lipid, a steroid or a conjugate of these (e.g., a glycoprotein, a lipoprotein, a glycolipid). In certain instances the biospecific adsorbent can be a macromolecular structure such as a multiprotein complex, a biological membrane or a virus. Biospecific adsorbents typically have higher specificity for a target analyte than chromatographic adsorbents. Further examples of adsorbents for use in SELDI can be found in U.S. Pat. No. 6,225,047 (Hutchens and Yip, "Use of retentate chromatography to generate difference maps," May 1, 2001). In some embodiments, a SEAC probe is provided as a pre-activated surface, which can be modified to provide an adsorbent of choice. For example, certain probes are provided with a reactive moiety that is capable of binding a biological molecule through a covalent bond. Epoxide and carbodiimidizole are useful reactive moieties to covalently bind biospecific adsorbents such as antibodies or cellular receptors.

"Affybody" or "Affibody®" refers to a small robust protein, derived from a bacterial receptor structure, which may be engineered to bind to virtually any molecular moiety. Affibodies are commercially available through Affibody, Teknikringen 30, floor 6, Box 700 04, Stockholm SE-10044, Sweden, Phone: 46-08-790-6595, FAX: 46-08-790-6538, and are the subject of U.S. Pat. No. 5,831,012.

The phrase "specifically binds" refers to a binding reaction that is determinative of the presence of an epitope in a heterogeneous population of biological molecules. A molecule is said to specifically bind to an epitope when the molecule binds at least twice the molar amount, more typically 10 to 100 times the molar amount of background molecules. For example, solid-phase ELISA immunoassays are routinely used to select antibodies that specifically bind with an epitope of an antigen (see, e.g., Harlow & Lane, *Antibodies, A Laboratory Manual* (1988), for a description of immunoassay formats and conditions that can be used to determine specific binding). In an ELISA format, and antibody specifically binding an epitope will produce at least twice background signal and more typically more than 10 to 100 times background signal.

In a preferred embodiment affinity mass spectrometry involves applying a liquid sample comprising an analyte to the adsorbent surface of a SELDI probe. Analytes, such as polypeptides, having affinity for the adsorbent bind to the probe surface. Typically, the surface is then washed to remove unbound molecules, and leaving retained molecules. The extent of analyte retention is a function of the stringency of the wash used. An energy absorbing material (e.g., matrix) is then applied to the adsorbent surface. Retained molecules are then detected by laser desorption/ionization mass spectrometry.

SELDI is useful for protein profiling, in which proteins in a sample are detected using one or several different SELDI surfaces. In turn, protein profiling is useful for difference mapping, in which the protein profiles of different samples are compared to detect differences in protein expression between the samples.

"Adsorption" refers to detectable non-covalent binding of an analyte to an adsorbent or capture reagent.

"Surface-Enhanced Neat Desorption" or "SEND" is a version of SELDI that involves the use of probes ("SEND probe") comprising a layer of energy absorbing molecules attached to the probe surface. Attachment can be, for example, by covalent or non-covalent chemical bonds. Unlike traditional MALDI, the analyte in SEND is not trapped within a crystalline matrix of energy absorbing molecules for desorption/ionization. "Energy absorbing molecules" ("EAM") refer to molecules that are capable of absorbing energy from a laser desorption/ionization source and thereafter contributing to desorption and ionization of analyte molecules in contact therewith. The phrase includes molecules used in MALDI, frequently referred to as "matrix", and explicitly includes cinnamic acid derivatives, sinapinic acid ("SPA"), cyano-hydroxy-cinnamic acid ("CHCA") and dihydroxybenzoic acid, ferulic acid, hydroxyacetophenone derivatives, as well as others. It also includes EAMs used in SELDI. In certain embodiments, the energy absorbing molecule is incorporated into a linear or cross-linked polymer, e.g., a polymethacrylate. For example, the composition can be a co-polymer of α-cyano-4-methacryloyloxycinnamic acid and acrylate. In another embodiment, the composition is a co-polymer of α-cyano-4-methacryloyloxycinnamic acid, acrylate and 3-(tri-methoxy)silyl propyl methacrylate. In another embodiment, the composition is a co-polymer comprising α-cyano-4-methacryloyloxycinnamic acid and octadecylmethacrylate ("C18 SEND"). SEND is further described in U.S. Pat. No. 5,719,060 and U.S. patent application No. 60/408,255, filed Sep. 4, 2002 (Kitagawa, "Monomers And Polymers Having Energy Absorbing Moieties Of Use In Desorption/Ionization Of Analytes").

"Surface-Enhanced Photolabile Attachment and Release" or "SEPAR" is a version of SELDI that involves the use of probes having moieties attached to the surface that can covalently bind an analyte, and then release the analyte through breaking a photolabile bond in the moiety after exposure to light, e.g., laser light. SEPAR is further described in U.S. Pat. No. 5,719,060.

SEAC/SEND is a version of SELDI in which both a capture reagent and an energy absorbing molecule are attached to the sample presenting surface. SEAC/SEND probes therefore allow the capture of analytes through affinity capture and desorption without the need to apply external matrix. The C18 SEND biochip is a version of SEAC/SEND, comprising a C18 moiety which functions as a capture reagent, and a CHCA moiety, which functions as an energy absorbing moiety.

"Eluant" or "wash solution" refers to an agent, typically a solution, which is used to affect or modify adsorption of an analyte to an adsorbent surface and/or remove unbound materials from the surface. The elution characteristics of an eluant can depend, for example, on pH, ionic strength, hydrophobicity, degree of chaotropism, detergent strength and temperature.

"Analyte" refers to any component of a sample that is desired to be detected. The term can refer to a single component or a plurality of components in the sample.

The "complexity" of a sample adsorbed to an adsorption surface of an affinity capture probe means the number of different protein species that are adsorbed.

"Molecular binding partners" and "specific binding partners" refer to pairs of molecules, typically pairs of biomolecules that exhibit specific binding. Molecular binding partners include, without limitation, receptor and ligand, antibody and antigen, biotin and avidin, and biotin and streptavidin.

"Multicomponent biological complex" refers to any biomolecular complex comprising two or more components being encoded by different genetic elements including different genes, reading frames of the same nucleotide sequence, having different molecular weights or volumes, undergoing variant post-transcriptional processing including products of different mRNA splices variants, or belong to different classes of biomolecules, the classes being proteins, simple sugars, carbohydrates, lipids and fats, and nucleotides and nucleic acids.

"Small organic molecule" refers to organic molecules of a size comparable to those organic molecules generally used in pharmaceuticals. Small organic molecules as used herein typically range in size up to about 5000 Da, up to about 2500 Da, up to about 2000 Da, or up to about 1000 Da.

An "equilibration wash" or "initial wash solution" refers to a wash solution designed to remove only those fractions of the sample that are bound adventitiously (usually meaning bound via a mechanism other than that for which the application was designed) or not bound at all. Typically an initial wash solution will be of physiologic ionic strength and pH at room temperature. By contrast, an "elution wash solution" is a wash solution designed to dissociate part of, or all of the sample bound to the solid support. "Elution washes" typically have ionic strengths and/or pH values that are different from physiologic or have additional components designed to disrupt biomolecular interactions (i.e., they are more stringent solutions than the initial wash solution). Typical additional components that disrupt biomolecular interactions include, but are not limited to, chaotropic salts, glycerol, multivalent ions, including zwitterions, and ampholytic reagents.

"Stringent," in the context of this invention, refers to the disruptive nature of a given solution towards some or all of the biomolecular interactions present in a given multi-subunit complex. Increasing the stringency of a solution, for example, refers to altering its composition in a manner that could disrupt biomolecular interactions of a multi-subunit complex; i.e. altering the chemical and/or physical nature of the solution away from the conditions present for the "initial wash solution".

"pH-Based Eluants" are eluants that modify the selectivity of the adsorbent based upon pH (i.e., charge). They include known pH buffers, acidic solutions, and basic solutions. By washing an analyte bound to a given adsorbent with a particular pH buffer, the charge can be modified and therefore the strength of the bond between the adsorbent and the analyte in the presence of the particular pH buffer can be challenged. Those analytes that are less competitive than others for the adsorbent at the pH of the eluant will be desorbed from the adsorbent and eluted, leaving bound only those analytes which bind more strongly to the adsorbent at the pH of the eluant. The stringency of pH-based eluants depends on the concentration of acid or base.

"Ionic Strength-Based eluants" are eluants that modify the selectivity of the adsorbent with respect to ionic strength include salt solutions of various types and concentrations. The amount of salt solubilized in the eluant solution affects the ionic strength of the eluant and modifies the adsorbent binding ability correspondingly. Eluants containing a low concentration of salt provide a slight modification of the adsorbent binding ability with respect to ionic strength. Eluants containing a high concentration of salt provide a greater modification of the adsorbent binding ability with respect to ionic strength.

"Water Structure-Based eluants" are eluants that modify the selectivity of the adsorbent by alteration of water structure or concentration include urea and chaotropic salt solutions. Typically, urea solutions include, e.g., solutions ranging in concentration from 0.1 to 8 M. Chaotropic salts which can be used to provide eluants include sodium thiocyanate. Water structure-based eluants modify the ability of the adsorbent to bind the analyte due to alterations in hydration or bound water structure. Eluants of this type include for example, glycerol, ethylene glycol and organic solvents. Chaotropic anions increase the water solubility of nonpolar moieties thereby decreasing hydrophobic interactions between the analyte and the adsorbent.

"Detergent-Based eluants" are eluants that modify the selectivity of the adsorbent with respect to surface tension and analyte structure include detergents and surfactants. Suitable detergents for use as eluants include ionic and nonionic detergents such as CHAPS, TWEEN and NP-40. Detergent-based eluants modify the ability of the adsorbent to bind the analyte as the hydrophobic interactions are modified when the hydrophobic and hydrophilic groups of the detergent are introduced. Hydrophobic interactions between the analyte and the adsorbent, and within the analyte are modified and charge groups are introduced, e.g., protein denaturation with ionic detergents such as SDS.

"Hydrophobicity-Based eluants" are eluants that modify the selectivity of the adsorbent with respect to dielectric constant are those eluants which modify the selectivity of the adsorbent with respect to hydrophobic interaction. Examples of suitable eluants that function in this capacity include organic solvents (e.g., propanol, acetonitrile, ethylene glycol and glycerol), thiophilic salts (e.g., ammonium sulfate), and detergents such as those mentioned above. Use of acetonitrile as eluant is typical in reverse phase chromatography. Inclusion of ethylene glycol in the eluant is effective in eluting immunoglobulins from salt-promoted interactions with thiophilic adsorbents.

"Monitoring" refers to recording changes in a continuously varying parameter.

Protein biochips produced by Ciphergen Biosystems comprise surfaces having chromatographic or biospecific adsorbents attached thereto at addressable locations. Ciphergen ProteinChip® arrays include NP20, H4, H50, SAX-2, Q10, WCX-2, CM10, IMAC-3, IMAC30, LSAX-30, LWCX-30, IMAC-40, PS-10, PS-20 and PG-20. These protein biochips comprise an aluminum substrate in the form of a strip. The surface of the strip is coated with silicon dioxide.

In the case of the NP-20 biochip, silicon oxide functions as a hydrophilic adsorbent to capture hydrophilic proteins.

H4, H50, SAX-2, Q10, WCX-2, CM10, IMAC-3, IMAC30, PS-10 and PS-20 biochips further comprise a functionalized, cross-linked polymer in the form of a hydrogel physically attached to the surface of the biochip or covalently attached through a silane to the surface of the biochip. The H4 biochip has isopropyl functionalities for hydrophobic binding. The H50 biochip has nonylphenoxy-poly(ethylene glycol)methacrylate for hydrophobic binding. The SAX-2 and Q10 biochips have quaternary ammonium functionalities for anion exchange. The WCX-2 and CM10 biochips have carboxylate functionalities for cation exchange. The IMAC-3 and IMAC30 biochips have nitrilo-acetic acid functionalities that adsorb transition metal ions, such as $Cu^{++}$ and $Ni^{++}$, by chelation. These immobilized metal ions allow adsorption of peptide and proteins by coordinate bonding. The PS-10 biochip has carbodiimidizole functional groups that can react with groups on proteins for covalent binding. The PS-20 biochip has epoxide functional groups for covalent binding with proteins. The PS-series biochips are useful for binding biospecific adsorbents, such as antibodies, receptors, lectins, heparin, Protein A, biotin/streptavidin and the like, to chip surfaces where they function to specifically capture analytes from a sample. The PG-20 biochip is a PS-20 chip to which Protein G is attached. The LSAX-30 (anion exchange), LWCX-30 (cation exchange) and IMAC-40 (metal chelate) biochips have functionalized latex beads on their surfaces. Such biochips are further described in: WO 00/66265 (Rich et al., "Probes for a Gas Phase Ion Spectrometer," Nov. 9, 2000); WO 00/67293 (Beecher et al., "Sample Holder with Hydrophobic Coating for Gas Phase Mass Spectrometer," Nov. 9, 2000); U.S. patent application Ser. No. 09/908,518 (Pohl et al., "Latex Based Adsorbent Chip," Jul. 16, 2002) and U.S. patent application No. 60/350,110 (Um et al., "Hydrophobic Surface Chip," Nov. 8, 2001).

Upon capture on a biochip, analytes can be detected by a variety of detection methods selected from, for example, a gas phase ion spectrometry method, an optical method, an electrochemical method, atomic force microscopy and a radio frequency method. Gas phase ion spectrometry methods are described herein. Of particular interest is the use of mass spectrometry and, in particular, SELDI. Optical methods include, for example, detection of fluorescence, luminescence, chemiluminescence, absorbance, reflectance, transmittance, birefringence or refractive index (e.g., surface plasmon resonance, ellipsometry, a resonant mirror method, a grating coupler waveguide method or interferometry). Optical methods include microscopy (both confocal and non-confocal), imaging methods and non-imaging methods. Immunoassays in various formats (e.g., ELISA) are popular methods for detection of analytes captured on a solid phase. Electrochemical methods include voltametry and amperometry methods. Radio frequency methods include multipolar resonance spectroscopy.

Data generation in mass spectrometry begins with the detection of ions by an ion detector. A typical laser desorption mass spectrometer can employ a nitrogen laser at 337.1 nm. A useful pulse width is about 4 nanoseconds. Generally, power output of about 1-25 µJ is used. Ions that strike the detector generate an electric potential that is digitized by a high-speed time-array recording device that digitally captures the analog signal. Ciphergen's ProteinChip® system employs an analog-to-digital converter (ADC) to accomplish this. The ADC integrates detector output at regularly spaced time intervals into time-dependent bins. The time intervals typically are one to four nanoseconds long. Furthermore, the time-of-flight spectrum ultimately analyzed typically does not represent the signal from a single pulse of ionizing energy against a sample, but rather the sum of signals from a number of pulses. This reduces noise and increases dynamic range. This time-of-flight data is then subject to data processing. In Ciphergen's ProteinChip® software, data processing typically includes TOF-to-M/Z transformation, baseline subtraction, high frequency noise filtering.

TOF-to-M/Z transformation involves the application of an algorithm that transforms times-of-flight into mass-to-charge ratio (M/Z). In this step, the signals are converted from the time domain to the mass domain. That is, each time-of-flight is converted into mass-to-charge ratio, or M/Z. Calibration can be done internally or externally. In internal calibration, the sample analyzed contains one or more analytes of known M/Z. Signal peaks at times-of-flight representing these massed analytes are assigned the known M/Z. Based on these assigned M/Z ratios, parameters are calculated for a mathematical function that converts times-of-flight to M/Z. In external calibration, a function that converts times-of-flight to M/Z, such as one created by prior internal calibration, is applied to a time-of-flight spectrum without the use of internal calibrants.

Baseline subtraction improves data quantification by eliminating artificial, reproducible instrument offsets that perturb the spectrum. It involves calculating a spectrum baseline using an algorithm that incorporates parameters such as peak width, and then subtracting the baseline from the mass spectrum.

High frequency noise signals are eliminated by the application of a smoothing function. A typical smoothing function applies a moving average function to each time-dependent bin. In an improved version, the moving average filter is a variable width digital filter in which the bandwidth of the filter varies as a function of, e.g., peak bandwidth, generally becoming broader with increased time-of-flight. See, e.g., WO 00/70648, Nov. 23, 2000 (Gavin et al., "Variable Width Digital Filter for Time-of-flight Mass Spectrometry").

A computer can transform the resulting spectrum into various formats for displaying. In one format, referred to as "spectrum view or retentate map," a standard spectral view can be displayed, wherein the view depicts the quantity of analyte reaching the detector at each particular molecular weight. In another format, referred to as "peak map," only the peak height and mass information are retained from the spectrum view, yielding a cleaner image and enabling analytes with nearly identical molecular weights to be more easily seen. In yet another format, referred to as "gel view," each mass from the peak view can be converted into a grayscale image based on the height of each peak, resulting in an appearance similar to bands on electrophoretic gels. In yet another format, referred to as "3-D overlays," several spectra can be overlaid to study subtle changes in relative peak heights. In yet another format, referred to as "difference map view," two or more spectra can be compared, conveniently highlighting unique analytes and analytes that are up- or down-regulated between samples.

Analysis generally involves the identification of peaks in the spectrum that represent signal from an analyte. Peak selection can, of course, be done visually. However, software is available as part of Ciphergen's ProteinChip® software that can automate the detection of peaks. In general, this software functions by identifying signals having a signal-to-noise ratio above a selected threshold and labeling the mass of the peak at the centroid of the peak signal. In one useful application many spectra are compared to identify identical peaks present in some selected percentage of the mass spectra. One version of this software clusters all peaks appearing in the various spectra within a defined mass range, and assigns a mass (M/Z) to all the peaks that are near the mid-point of the mass (M/Z) cluster.

Peak data from one or more spectra can be subject to further analysis by, for example, creating a spreadsheet in which each row represents a particular mass spectrum, each column represents a peak in the spectra defined by mass, and each cell includes the intensity of the peak in that particular spectrum. Various statistical or pattern recognition approaches can applied to the data.

The spectra that are generated in embodiments of the invention can be classified using a pattern recognition process that uses a classification model. In general, the spectra will represent samples from at least two different groups for which a classification algorithm is sought. For example, the groups can be pathological v. non-pathological (e.g., cancer v. non-cancer), drug responder v. drug non-responder, toxic response v. non-toxic response, progressor to disease state v. non-progressor to disease state, phenotypic condition present v. phenotypic condition absent.

In some embodiments, data derived from the spectra (e.g., mass spectra or time-of-flight spectra) that are generated using samples such as "known samples" can then be used to "train" a classification model. A "known sample" is a sample that is pre-classified. The data that are derived from the spectra and are used to form the classification model can be referred to as a "training data set". Once trained, the classification model can recognize patterns in data derived from spectra generated using unknown samples. The classification model can then be used to classify the unknown samples into classes. This can be useful, for example, in predicting whether or not a particular biological sample is associated with a certain biological condition (e.g., diseased vs. non diseased).

The training data set that is used to form the classification model may comprise raw data or pre-processed data. In some embodiments, raw data can be obtained directly from time-of-flight spectra or mass spectra, and then may be optionally "pre-processed" as described above.

Classification models can be formed using any suitable statistical classification (or "learning") method that attempts to segregate bodies of data into classes based on objective parameters present in the data. Classification methods may be either supervised or unsupervised. Examples of supervised and unsupervised classification processes are described in Jain, "Statistical Pattern Recognition: A Review", IEEE Transactions on Pattern Analysis and Machine Intelligence, Vol. 22, No. 1, January 2000, which is herein incorporated by reference in its entirety.

In supervised classification, training data containing examples of known categories are presented to a learning mechanism, which learns one more sets of relationships that define each of the known classes. New data may then be applied to the learning mechanism, which then classifies the new data using the learned relationships. Examples of supervised classification processes include linear regression processes (e.g., multiple linear regression (MLR), partial least squares (PLS) regression and principal components regression (PCR)), binary decision trees (e.g., recursive partitioning processes such as CART—classification and regression trees), artificial neural networks such as back-propagation networks, discriminant analyses (e.g., Bayesian classifier or Fischer analysis), logistic classifiers, and support vector classifiers (support vector machines).

A preferred supervised classification method is a recursive partitioning process. Recursive partitioning processes use recursive partitioning trees to classify spectra derived from unknown samples. Further details about recursive partitioning processes are in U.S. Provisional Patent Application No. 60/249,835, filed on Nov. 16, 2000, and 60/254,746, filed on Dec. 11, 2000, and U.S. Non-Provisional patent application Ser. No. 09/999,081, filed Nov. 15, 2001, and Ser. No. 10/084,587, filed on Feb. 25, 2002. All of these U.S. Provisional and Non Provisional Patent Applications are herein incorporated by reference in their entirety for all purposes.

In other embodiments, the classification models that are created can be formed using unsupervised learning methods. Unsupervised classification attempts to learn classifications based on similarities in the training data set, without pre classifying the spectra from which the training data set was derived. Unsupervised learning methods include cluster analyses. A cluster analysis attempts to divide the data into "clusters" or groups that ideally should have members that are very similar to each other, and very dissimilar to members of other clusters. Similarity is then measured using some distance metric, which measures the distance between data items, and clusters together data items that are closer to each other. Clustering techniques include the MacQueen's K-means algorithm and the Kohonen's Self-Organizing Map algorithm.

The classification models can be formed on and used on any suitable digital computer. Suitable digital computers include micro, mini, or large computers using any standard or specialized operating system such as a Unix, Windows™ or Linux™ based operating system. The digital computer that is used may be physically separate from the mass spectrometer that is used to create the spectra of interest, or it may be coupled to the mass spectrometer.

The training data set and the classification models according to embodiments of the invention can be embodied by computer code that is executed or used by a digital computer. The computer code can be stored on any suitable computer readable media including optical or magnetic disks, sticks, tapes, etc., and can be written in any suitable computer programming language including C, C++, visual basic, etc.

All publications and patent applications cited in this specification are herein incorporated by reference as if each individual publication or patent application were specifically and individually indicated to be incorporated by reference.

Although the foregoing invention has been described in some detail by way of illustration and example for clarity and understanding, it will be readily apparent to one of ordinary skill in the art in light of the teachings of this invention that certain changes and modifications may be made thereto without departing from the spirit and scope of the appended claims.

As can be appreciated from the disclosure provided above, the present invention has a wide variety of applications. Accordingly, the following examples are offered for illustration purposes and are not intended to be construed as a limitation on the invention in any way. Those of skill in the art will readily recognize a variety of noncritical parameters that could be changed or modified to yield essentially similar results.

What is claimed is:

1. A method for creating a profile of interactions between components of at least one multicomponent biological complex in a sample, the method comprising, for each complex:
   (a) providing an aliquot from the sample, wherein the aliquot comprises the multicomponent biological complex;
   (b) immobilizing the multicomponent biological complex on a solid support through a biospecific affinity molecule, wherein the affinity molecule is not a nucleic acid, and wherein the affinity molecule binds a first component of the complex and wherein unbound material has been removed from the solid support;
   (c) washing the immobilized multicomponent biological complex with a sequence of elution washes, wherein a first solute in each elution wash, has a concentration such that the sequence of elation washes forms a gradient of increasing or decreasing concentration of the first solute; and
   (d) measuring for a second component of the complex in each of the elution washes; whereby the profile for the complex from the sample comprises the measurements from the elution washes.

2. The method of claim 1 wherein the sample is selected from the group consisting of tissue extracts, cell extracts, blood, urine, lymphatic fluid, in vitro protein expression media and derivatives thereof.

3. The method of claim 1 wherein the at least one complex is one complex.

4. The method of claim 1 wherein the at least one complex is a plurality of complexes, each bound through a biospecific affinity reagent.

5. The method of claim 1 wherein the affinity molecule is selected from the group consisting of: an antibody, a single chain antibody, a specific binding fragment of an antibody, an affibody, an enzyme, an enzyme substrate, a receptor, a receptor ligand, a drug, and an aptamer.

6. The method of claim 1 wherein the affinity molecule is immobilized to the solid support before binding the complex.

7. The method of claim 1 wherein the affinity molecule is bound to the solid support after binding the complex.

8. The method of claim 1 wherein the solid support is a chromatographic resin.

9. The method of claim 8 wherein the washes are performed in a non-flow-through device.

10. The method of claim 9, wherein the non-flow through device is a closed bottomed microtiter plate.

11. The method of claim 8 wherein the washes are performed in a flow-through device.

12. The method of claim 11 wherein the flow-through device is a microtiter drip plate, a flow-through column or a flow-through microcolumn.

13. The method of claim 1 wherein the solid support is a SELDI probe comprising the biospecific affinity molecule attached to the probe surface for capturing the complex.

14. The method of claim 1 wherein the unbound material is removed with an initial wash.

15. The method of claim 1 wherein the solute is selected from an ion, a salt, a detergent, a biomolecule or a binding competitor.

16. The method of claim 1, further comprising washing to immobilized multicomponent biological complex in a second aliquot of the sample with a second sequence of elution washes, wherein to second solute is different than to first solute.

17. The method of claim 1 wherein the second component is detected by an optical method, an electrochemical method, atomic force microscopy or a radio frequency method.

18. The method of claim 1 wherein the second component is detected by mass spectrometry.

19. The method of claim 18 wherein mass spectrometry is affinity mass spectrometry.

20. The method of claim 19 wherein affinity mass spectrometry comprises SEND.

21. The method of claim 1 further comprising after step (c), measuring components of the complex still immobilized on the support through the biospecific affinity molecule, whereby the profile further comprises the measurements of the complex.

22. A method comprising:
(a) providing a set of biological samples, wherein to set comprises at least two subsets, each subset characterized by a different biological characteristic;
(b) creating a profile of interactions between components of at least one multicomponent biological complex for each sample in the set, wherein the method comprises:
 (i) providing an aliquot from each sample, wherein the aliquot comprises the multicomponent biological complex;
 (ii) immobilizing the multicomponent biological complex on a solid support through a biospecific affinity molecule, wherein the affinity molecule is not a nucleic acid, and wherein the affinity molecule binds a first component of the complex and wherein unbound material has been removed from the solid supports;
 (iii) washing the immobilized complex with a plurality of successive elution washes, wherein the concentration of a solute in the successive elution washes form a gradient of increasing or decreasing concentration; and
 (iv) measuring a second component in the successive elution washes, whereby to profile for each sample in the set comprises the measurements from the elution washes from each aliquot; and
(c) comparing the profiles for each sample in the set to detect differences in interaction between components in each subset.

23. The method of claim 22 wherein the different biological characteristics are selected from the pairs consisting of: pathological and non-pathological, drug responder and drug non-responder, toxic response and non-toxic response, and progressor to disease state and non-progressor to disease state.

24. The method of claim 22 further comprising exposing the samples to be compared to different conditions, wherein one sample is exposed to an inhibitor RNA and the other sample is not exposed to the inhibitor RNA.

25. The method of claim 22 wherein step (b) further comprises, after step (iii) detecting components of the complex still immobilized on the support through the biospecific affinity molecule, whereby the profile further comprises the measurements from the support.

26. The method of claim 22, further comprising performing steps (b)(i)-(iv) on a second aliquot from each samples in the set, wherein the elution washes comprise a second, different solute and the concentrations of the second solute in the successive elution washes form a gradient of increasing or decreasing concentration.

27. The method of claim 22 wherein comparing comprises using the profiles to train a computerized learning algorithm, wherein the computerized learning algorithm generates a classification algorithm that classifies a profile into one of the at least two subsets.

28. A method for creating a profile of interactions between components of at least one multicomponent biological complex in a sample, the method comprising, for each complex:
(a) providing a plurality of aliquots from the sample, each aliquot comprising the same multicomponent biological complex;
(b) immobilizing the multicomponent biological complex on a solid support through a biospecific affinity molecule, wherein the affinity molecule is not a nucleic acid and wherein the affinity molecule binds a first component of the complex and wherein unbound material has been removed from the solid supports;
(c) washing the immobilized multicomponent biological complex in each of the aliquots with a sequence of citation washes, wherein a first solute in each elution wash has a concentration such that the sequence of elution washes forms a gradient of increasing or decreasing concentration of the first solute; and
(d) measuring at least one second component of the complex in each of the elution washes; whereby the profile for the sample comprises the measurements from the elution washes from each aliquot.

29. The method of claim 28 further comprising after step (c), detecting components of the complex still immobilized on the support through the biospecific affinity molecule, whereby the profile further comprises the measurements from the support.

30. The method of claim 28 further comprising performing step (c) on a second plurality of aliquots from the sample, wherein the elution washes comprise a second, different solute and the concentrations of the second solute in the successive elution washes form a gradient of increasing or decreasing concentration.

31. A method comprising:

(a) providing a set of biological samples, wherein the set comprises at least two subsets, each subset characterized by a different biological characteristic;
(b) creating a profile of interactions between components of at least one multicomponent biological complex for each sample in the set, wherein creating a profile for a complex in a sample comprises:
  (i) providing a plurality of aliquots from each sample in the set, each aliquot comprising the same multicomponent biological complex;
  (ii) immobilizing the multicomponent biological complex on a solid support through a biospecific affinity molecule, wherein the affinity molecule is not a nucleic, acid and wherein the affinity molecule binds a first component of the complex and wherein unbound material has been removed from the solid supports;
  (iii) washing the immobilized complex in each of the aliquots with an elution wash of a first sequence of elution washes, wherein the concentrations of a first solute in the elution washes of the sequence form a gradient of increasing or decreasing concentration; and
  (iv) measuring at least one second component of the complex in each of the elution washes; whereby the profile for a complex in the set comprises the measurements from the elution washes from each aliquot; and
(c) comparing the profiles for the samples to detect differences in interaction between components in the samples.

32. The method of claim 31 further comprising washing the immobilized complex in a second plurality of aliquots from each sample with one elution wash of a second set of elation washes, wherein the concentrations of a second solute in each member of the set of elution washes form a gradient of increasing or decreasing concentration, and wherein the second solute is different than the solute.

33. The method of claim 31 wherein step (b) further comprises, after step (iii) detecting components of the complex still immobilized on the support through the biospecific affinity molecule, whereby the profile further comprises the measurements from the support.

34. The method of claim 31 further comprising performing steps (b), (i)-(iv) on a second plurality of aliquots from the set, wherein the elution washes comprise a second, different solute and the concentrations of the second solute in the successive elution washes form a gradient of increasing or decreasing concentration.

35. The method of claim 32 wherein comparing the profiles for the set detects differences in interaction between components in the samples.

* * * * *